US012578299B2

(12) United States Patent
Murakami et al.

(10) Patent No.: US 12,578,299 B2
(45) Date of Patent: Mar. 17, 2026

(54) SENSOR ELEMENT AND GAS SENSOR

(71) Applicant: NGK INSULATORS, LTD., Aichi (JP)

(72) Inventors: Yuta Murakami, Nagoya (JP); Keita Kayano, Nagoya (JP); Akari Yamada, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 414 days.

(21) Appl. No.: 18/157,853

(22) Filed: Jan. 23, 2023

(65) Prior Publication Data

US 2023/0152269 A1 May 18, 2023

Related U.S. Application Data

(63) Continuation of application No. PCT/JP2022/012184, filed on Mar. 17, 2022.

(Continued)

(51) Int. Cl.
*G01N 27/407* (2006.01)
*G01N 25/16* (2006.01)
(Continued)

(52) U.S. Cl.
CPC ......... *G01N 27/4077* (2013.01); *G01N 25/16* (2013.01); *G01N 27/4062* (2013.01);
(Continued)

(58) Field of Classification Search
CPC ........... G01N 27/4077; G01N 27/4062; G01N 27/4067; G01N 27/409; G01N 33/0036;
(Continued)

(56) References Cited

U.S. PATENT DOCUMENTS

| | | | |
|---|---|---|---|
| 2016/0161445 A1 | 6/2016 | Sakakibara et al. | |
| 2018/0284055 A1* | 10/2018 | Hino .................. | G01N 27/4072 |

(Continued)

FOREIGN PATENT DOCUMENTS

| | | |
|---|---|---|
| JP | 2016-109685 A | 6/2016 |
| JP | 2020-106395 A | 7/2020 |

(Continued)

OTHER PUBLICATIONS

International Preliminary Report on Patentability received in corresponding International Application No. PCT/JP2022/012184 dated Dec. 28, 2023.

(Continued)

*Primary Examiner* — James Lin
*Assistant Examiner* — Vivian A Tran
(74) *Attorney, Agent, or Firm* — MATTINGLY & MALUR, PC

(57) ABSTRACT

A sensor element for detecting a specific gas concentration in a measurement-object gas, the sensor element includes; an elongate element body that includes a solid electrolyte layer and has a shape including at least one side surface extending in a longitudinal direction; a dense layer that is disposed on the side surface; and an intermediate layer disposed at least between the dense layer and the element body, wherein, when thermal expansion coefficients of the solid electrolyte layer, the dense layer, and the intermediate layer in a temperature range of from 20° C. to 1360° C. are denoted by thermal expansion coefficients Ea, Eb, and Ec, respectively, a ratio Ea/Eb is more than 1.0 and 5.0 or less, and Ea>Ec>Eb is satisfied.

11 Claims, 7 Drawing Sheets

Related U.S. Application Data

(60) Provisional application No. 63/211,665, filed on Jun. 17, 2021.

(51) Int. Cl.

| | |
|---|---|
| *G01N 27/406* | (2006.01) |
| *G01N 27/409* | (2006.01) |
| *G01N 27/41* | (2006.01) |
| *G01N 33/00* | (2006.01) |

(52) U.S. Cl.
CPC ..... *G01N 27/4067* (2013.01); *G01N 27/4071* (2013.01); *G01N 27/4072* (2013.01); *G01N 27/409* (2013.01); *G01N 27/41* (2013.01); *G01N 33/0036* (2013.01)

(58) Field of Classification Search
CPC ....... G01N 27/407–4072; G01N 27/41; G01N 25/16
See application file for complete search history.

(56) References Cited

U.S. PATENT DOCUMENTS

| | | | |
|---|---|---|---|
| 2019/0285571 A1* | 9/2019 | Okamoto ........... | G01N 27/4071 |
| 2020/0049679 A1 | 2/2020 | Nakayama et al. | |
| 2020/0064301 A1 | 2/2020 | Nakayama et al. | |
| 2020/0064305 A1 | 2/2020 | Nakayama et al. | |
| 2020/0209185 A1 | 7/2020 | Watanabe et al. | |

FOREIGN PATENT DOCUMENTS

| | | | |
|---|---|---|---|
| WO | 2019/155865 | A1 | 8/2019 |
| WO | 2019/155866 | A1 | 8/2019 |
| WO | 2019/155867 | A1 | 8/2019 |

OTHER PUBLICATIONS

International Search Report of PCT/JP2022/012184 dated Jun. 7, 2022.

* cited by examiner

SENSOR ELEMENT AND GAS SENSOR

REFERENCE TO RELATED APPLICATIONS

This application is a continuation application of PCT/JP2022/012184, filed on Mar. 17, 2022, which claims the benefit of U.S. Provisional Patent Application No. 63/211,665, filed on Jun. 17, 2021, the entire contents of which are incorporated herein by reference.

BACKGROUND OF THE INVENTION

1. Field of the Invention

The present invention relates to a sensor element and a gas sensor.

2. Description of the Related Art

A sensor element that detects the concentration of a specific gas such as NOx in a measurement-object gas such as an exhaust gas of an automobile is a known art (for example, Patent Literature 1). The sensor element in Patent Literature 1 includes: an elongate element body; an outer electrode disposed on the upper surface of the element body; an outer lead portion; a connector electrode; and a porous layer that covers the outer electrode and the outer lead portion. The outer electrode, the outer lead portion, and the connector electrode are connected in this order and are electrically continuous with each other, and the connector electrode is electrically connected to the outside. The sensor element in Patent Literature 1 further includes a dense layer disposed so as to divide the porous layer in the longitudinal direction of the element body. The dense layer covers the outer lead portion. The dense layer does not easily allow moisture to pass therethrough. Therefore, even when moisture in the measurement-object gas moves through the porous layer by capillary action, the presence of the dense layer prevents the moisture from reaching the connector electrode. A method for producing the above sensor element that is described in Patent Literature 1 includes: forming electrodes, green porous layers, and green dense layers on a plurality of green ceramic sheets corresponding to the element body by screen printing; stacking the plurality of green ceramic sheets; and firing the stacked green ceramic sheets.

CITATION LIST

Patent Literature

PTL1: International Publication No. WO2019/155865

SUMMARY OF THE INVENTION

As for the sensor element including the dense layer as described in Patent Literature 1, cracking may occur in the sensor element. It is therefore desirable to reduce the occurrence of cracking in the sensor element.

The present invention has been made to solve the foregoing problem, and it is a main object to further reduce the occurrence of cracking in a sensor element.

To achieve the above main object, the present invention employs the following means.

The sensor element of the present invention is a sensor element for detecting a specific gas concentration in a measurement-object gas, the sensor element including: an elongate element body that includes a solid electrolyte layer and has a shape including at least one side surface extending in a longitudinal direction and forward and rear ends that are ends opposite to each other in the longitudinal direction; at least one connector electrode that is disposed on a rear side of any of the at least one side surface and provided for electrical continuity with the outside of the sensor element; a porous layer that has a porosity of 10% or more and covers at least a forward end side of the side surface on which the connector electrode is disposed; a dense layer that is disposed on the side surface so as to divide the porous layer in the longitudinal direction or to be located rearward of the porous layer, is located forward of the connector electrode, and has a porosity of less than 10%; and an intermediate layer disposed at least between the dense layer and the element body, wherein, when thermal expansion coefficients of the solid electrolyte layer, the dense layer, and the intermediate layer in a temperature range of from 20° C. to 1360° C. are denoted by thermal expansion coefficients Ea, Eb, and Ec, respectively, the ratio Ea/Eb is more than 1.0 and 5.0 or less, and Ea>Ec>Eb is satisfied.

The sensor element includes the solid electrolyte layer, the dense layer, and the intermediate layer. The ratio Ea/Eb of the thermal expansion coefficient Ea of the solid electrolyte layer to the thermal expansion coefficient Eb of the dense layer is more than 1.0 and 5.0 or less, and the thermal expansion coefficient of the solid electrolyte layer is relatively close to the thermal expansion coefficient of the dense layer. Moreover, the intermediate layer is present at least between the dense layer and the solid electrolyte layer, and the thermal expansion coefficient Ec of the intermediate layer satisfies Ea>Ec>Eb. Specifically, the intermediate layer whose thermal expansion coefficient Ec is between the thermal expansion coefficient of the solid electrolyte layer and the thermal expansion coefficient of the dense layer is present between them. Since the solid electrolyte layer, the dense layer, and the intermediate layer satisfy the above positional relation and the relations between the thermal expansion coefficients Ea to Ec, the intermediate layer reduces stress caused by the difference between the thermal expansion coefficient Ea of the solid electrolyte layer and the thermal expansion coefficient Eb of the dense layer when the sensor element is heated during use. When the stress is generated in the sensor element, cracking is likely to occur. However, in the above sensor element, since the stress is reduced, the occurrence of cracking is reduced.

In the sensor element of the present invention, when the mean value of the thermal expansion coefficient Ea and the thermal expansion coefficient Eb is denoted by Ed ($=(Ea+Eb)/2$), formula (1) below may be satisfied. In this case, the thermal expansion coefficient Ec is relatively close to the median Ed of the thermal expansion coefficients Ea and Eb. Specifically, the thermal expansion coefficient Ec is not excessively close to the thermal expansion coefficient Ea and not excessively close to the thermal expansion coefficient Eb. Therefore, the stress generated when the sensor element is heated is further reduced, and the occurrence of cracking is further reduced.

$$Ed-0.8\times(Ed-Eb)<Ec<Ed+0.8\times(Ea-Ed) \tag{1}$$

In the sensor element of the present invention, the ratio Ea/Eb may be 3.0 or less. In this case, the thermal expansion coefficient Ea of the solid electrolyte layer and the thermal expansion coefficient Eb of the dense layer are closer to each other, so that the occurrence of cracking in the sensor element is further reduced.

In the sensor element of the present invention, the intermediate layer may have a thickness T of 1 μm or more. In this case, the effect of the presence of the intermediate layer in reducing the occurrence of cracking in the sensor element is obtained more reliably. The thickness T of the intermediate layer may be 10 μm or less.

In the sensor element of the present invention, the solid electrolyte layer may contain zirconia as a main component, and the dense layer may contain alumina as a main component. The intermediate layer may contain zirconia and alumina. The main component as used herein means a component with the highest content and is specifically a component with the highest volume ratio.

In the sensor element of the present invention, the sensor element may include: a detection portion including a plurality of electrodes disposed on a forward end side of the element body and used to detect the specific gas concentration in the measurement-object gas; and an outer lead portion that is disposed on the side surface on which the connector electrode is disposed and provides electrical continuity between any of the plurality of electrodes and the connector electrode. The porous layer may cover at least part of the outer lead portion. In this case, the porous layer may fully cover a portion of the outer lead portion that is not covered with the dense layer. The sensor element of the present invention may include an outer electrode that is one of the plurality of electrodes included in the detection portion and that is electrically continuous with the connector electrode through the outer lead portion and disposed on the side surface on which the connector electrode is disposed. In this case, the porous layer may cover the outer electrode.

The gas sensor of the present invention includes the sensor element in any of the above modes. Therefore, the gas sensor has the same effect as the effect of the above-described sensor element of the present invention, e.g., the effect of reducing the occurrence of cracking in the sensor element.

DETAILED DESCRIPTION OF THE INVENTION

Figure 1:
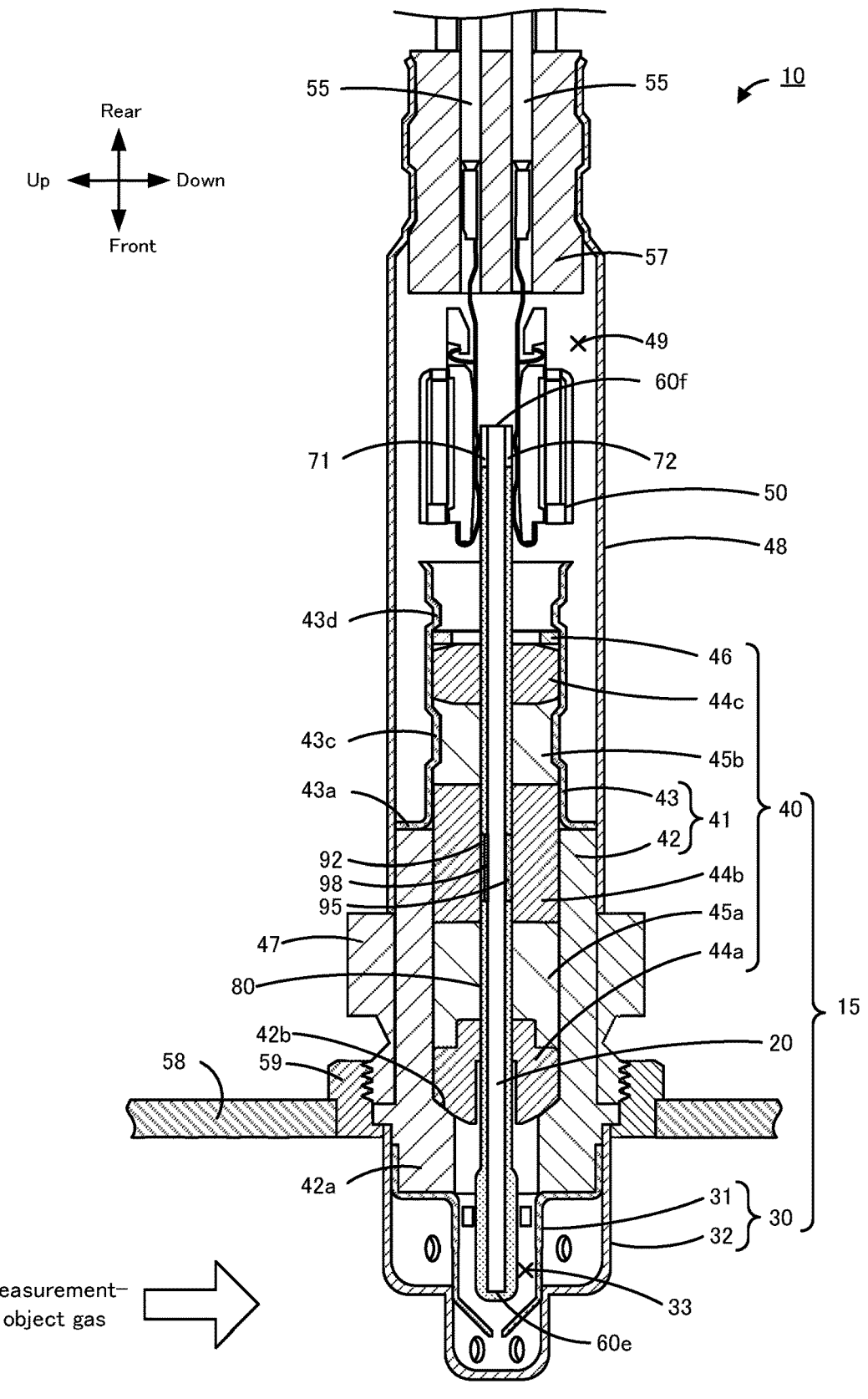
FIG. 1 is a cross-sectional view showing the manner of attaching a gas sensor 10 to a pipe 58.
Figure 2:
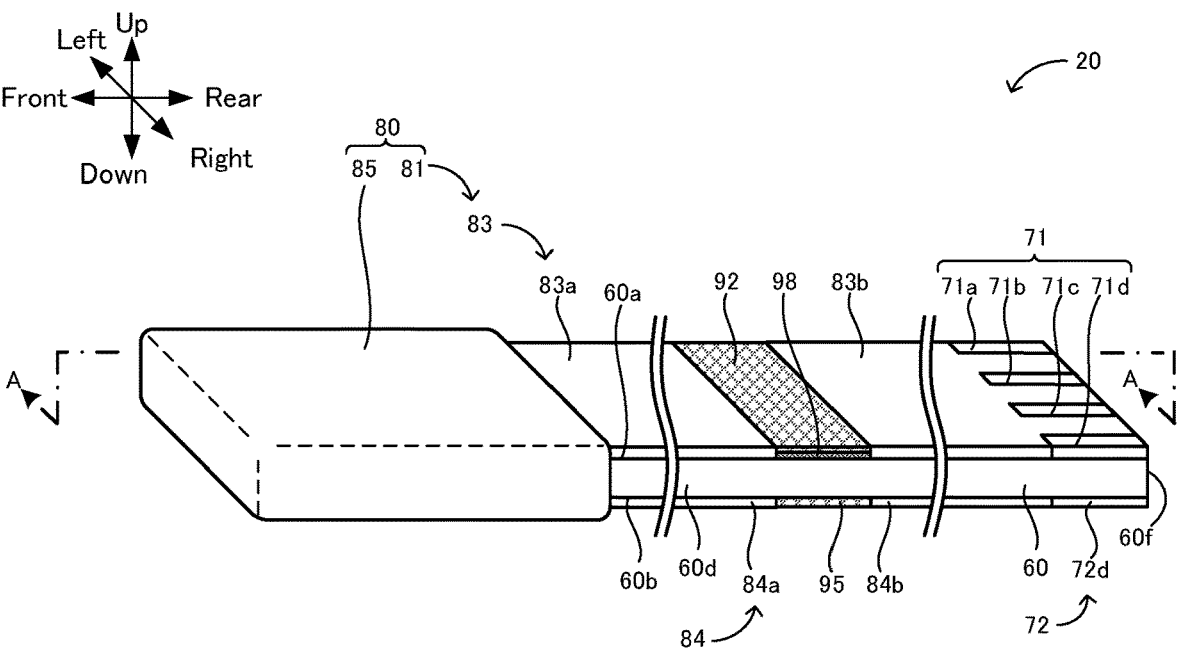
FIG. 2 is a perspective view of a sensor element 20.
Figure 3:
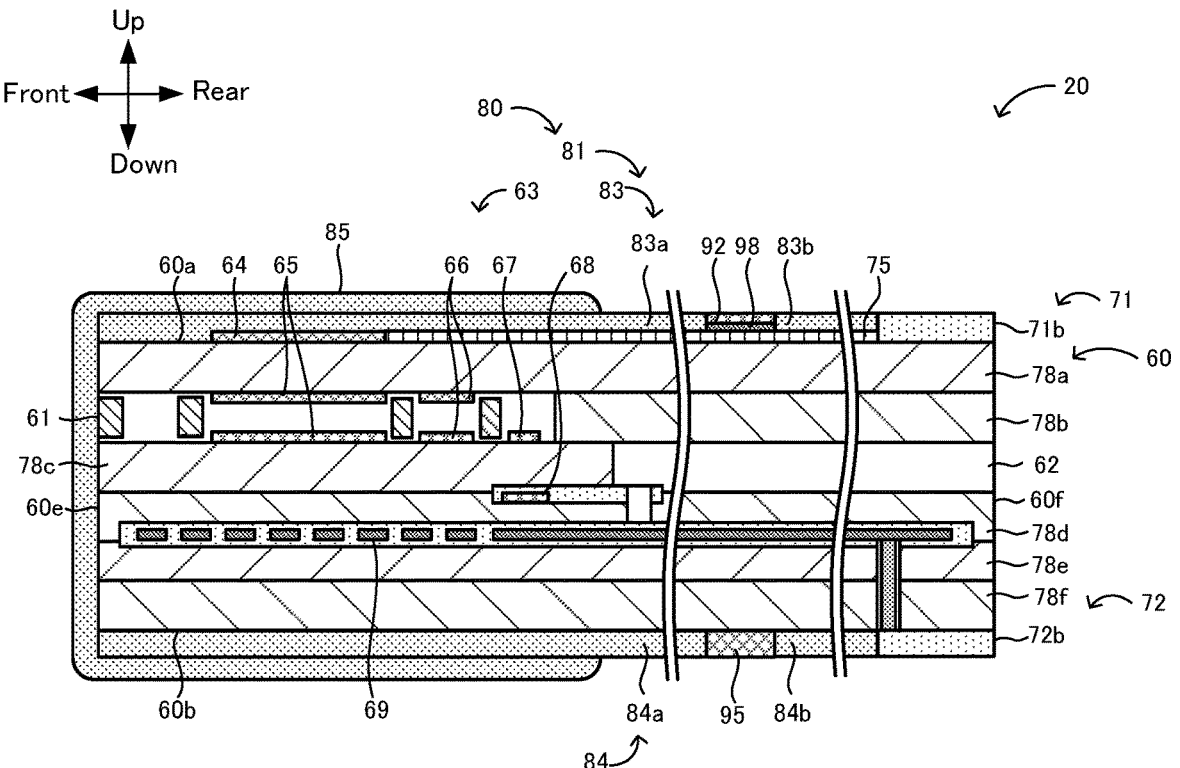
FIG. 3 is a cross-sectional view taken along A-A in FIG. 2.
Figure 4:
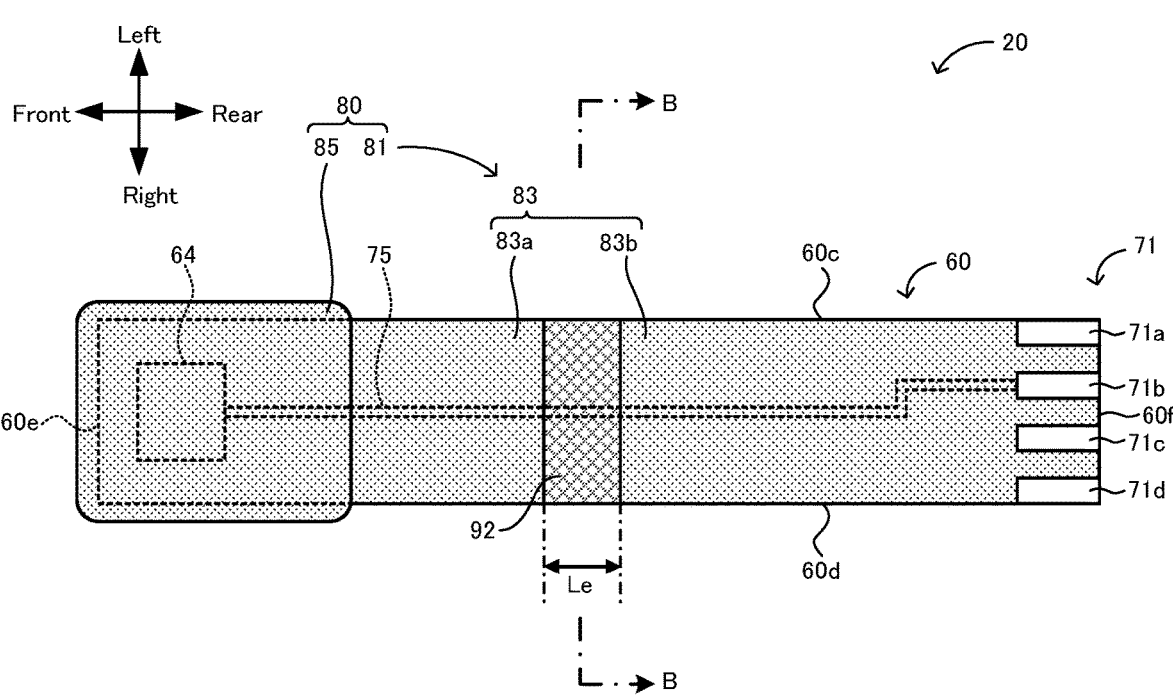
FIG. 4 is a top view of the sensor element 20.
Figure 5:
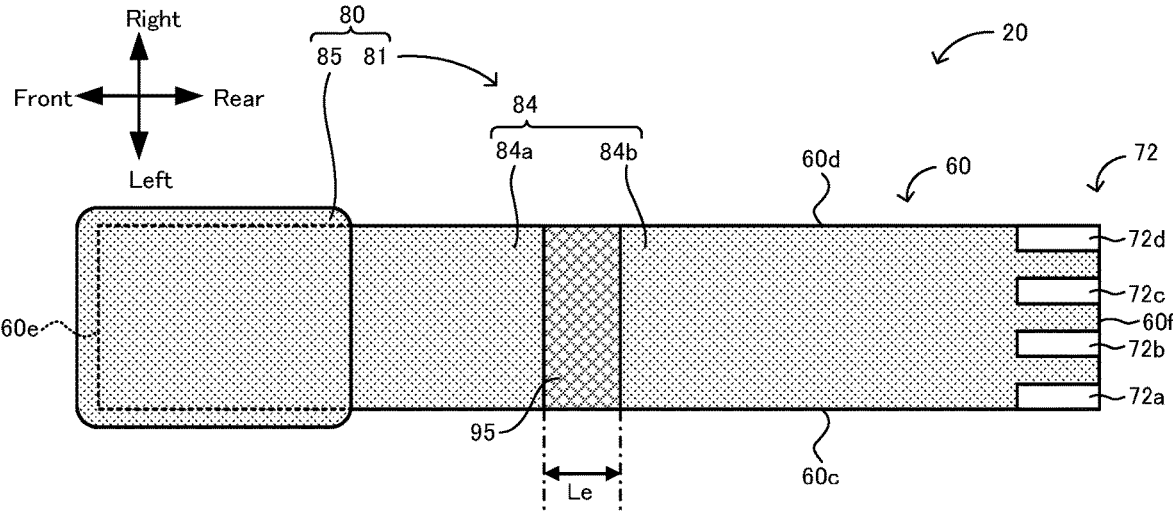
FIG. 5 is a bottom view of the sensor element 20.
Figure 6:
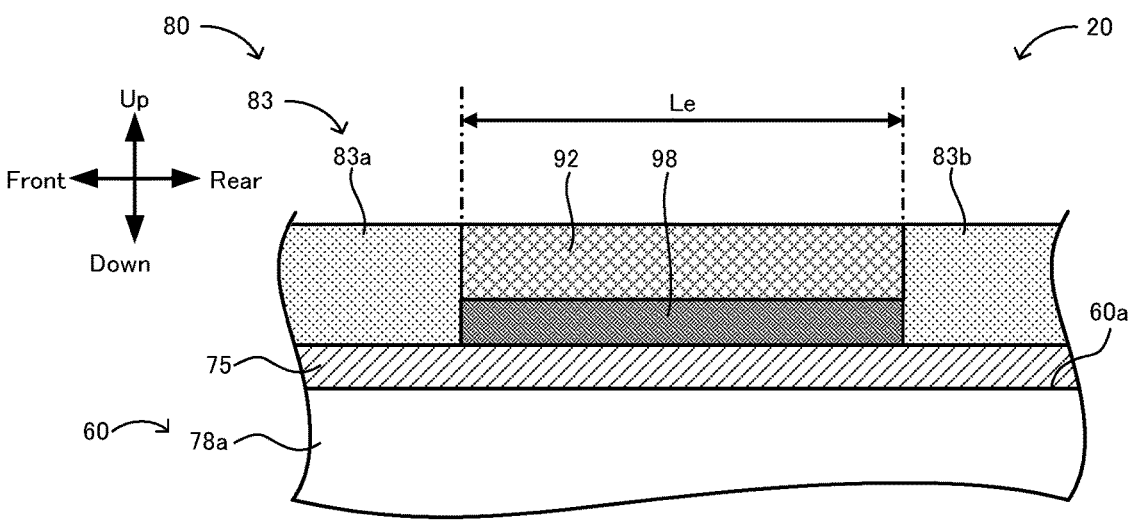
FIG. 6 is an enlarged view around an intermediate layer 98 in FIG. 3.
Figure 7:
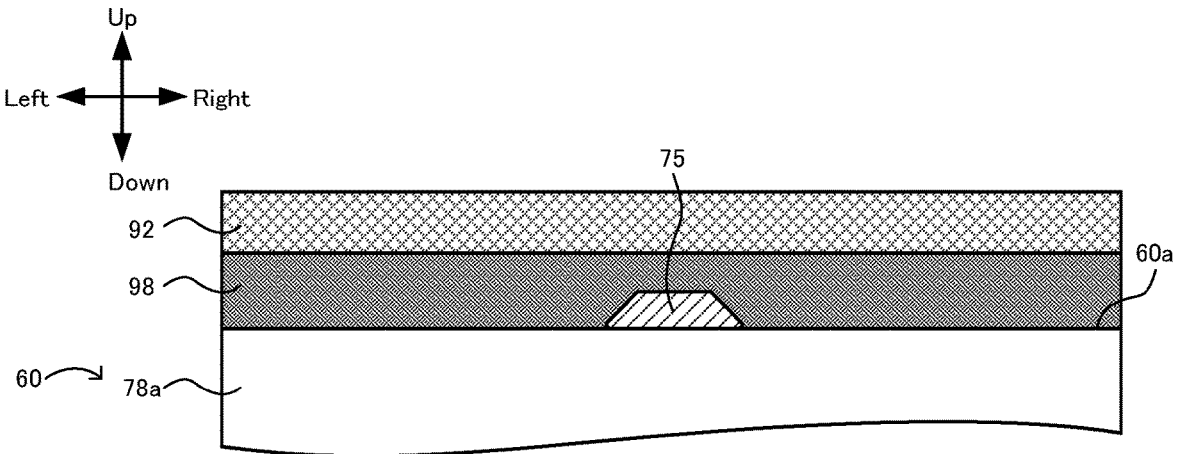
FIG. 7 is a partial cross-sectional view around the intermediate layer 98 in a cross-section taken along B-B in FIG. 4.

Next, embodiments of the present invention will be described using the drawings. FIG. 1 is a vertical cross-sectional view showing the manner of attaching, to a pipe 58, a gas sensor 10 including a sensor element 20 in an embodiment of the present invention. FIG. 2 is a perspective view of the sensor element 20 when it is viewed from the upper right front. FIG. 3 is a cross-sectional view taken along A-A in FIG. 2. FIG. 4 is a top view of the sensor element 20. FIG. 5 is a bottom view of the sensor element 20. FIG. 6 is an enlarged view around an intermediate layer 98 in FIG. 3. FIG. 7 is a partial cross-sectional view around the intermediate layer 98 in a cross-section taken along B-B in FIG. 4. In the present embodiment, as shown in FIGS. 2 and 3, the longitudinal direction of an element body 60 of the sensor element 20 is defined as a forward-rearward direction (lengthwise direction) of the element body 60, and the stacking direction (thickness direction) of the element body 60 is defined as an upward-downward direction. A direction perpendicular to the forward-rearward direction and the upward-downward direction is defined as a left-right direction (width direction).

As shown in FIG. 1, the gas sensor 10 includes an assembly 15, a bolt 47, an external cylinder 48, a connector 50, lead wires 55, and a rubber stopper 57. The assembly 15 includes the sensor element 20, a protective cover 30, and an element-sealing member 40. The gas sensor 10 is attached to the pipe 58 such as an exhaust gas pipe of a vehicle and used to measure the concentration of a specific gas (a specific gas concentration) such as NOx or $O_2$ contained in the exhaust gas used as a measurement-object gas. In the present embodiment, the gas sensor 10 measures the concentration of NOx as the specific gas concentration. The sensor element 20 has opposite ends (forward and rear ends) in the longitudinal direction, and the forward end side is the side exposed to the measurement-object gas.

As shown in FIG. 1, the protective cover 30 includes a bottomed cylindrical inner protective cover 31 that covers the forward end side of the sensor element 20 and a bottomed cylindrical outer protective cover 32 that covers the inner protective cover 31. A plurality of holes for allowing circulation of the measurement-object gas are formed in each of the inner and outer protective covers 31 and 32. An element chamber 33 is formed as a space surrounded by the inner protective cover 31, and a fifth surface 60e (forward end surface) of the sensor element 20 is disposed inside the element chamber 33.

The element-sealing member 40 is a member for sealing and fixing the sensor element 20. The element-sealing member 40 includes: a cylindrical member 41 including a main metal fitting 42 and an inner cylinder 43; insulators 44a to 44c; powder compacts 45a and 45b; and a metal ring 46. The sensor element 20 is located on the center axis of the element-sealing member 40 and pierces through the element-sealing member 40 in the forward-rearward direction.

The main metal fitting 42 is a cylindrical metallic member. The main metal fitting 42 has a thick-walled portion 42a located on the forward side and having an inner diameter smaller than that of the rear side. The protective cover 30 is attached to a portion of the main metal fitting 42 that is on the same side as the forward end of the sensor element 20 (i.e., the forward side). The rear end of the main metal fitting 42 is welded to a flange portion 43a of the inner cylinder 43. A part of the inner circumferential surface of the thick-walled portion 42a is formed as a bottom surface 42b that is a step surface. The bottom surface 42b bears the insulator 44a such that the insulator 44a does not protrude forward.

The inner cylinder 43 is a cylindrical metallic member and has the flange portion 43a at its forward end. The inner cylinder 43 and the main metal fitting 42 are welded and fixed to each other so as to be coaxial with each other. The inner cylinder 43 has a reduced diameter portion 43*c* for pressing the powder compact 45*b* in a direction toward the center axis of the inner cylinder 43 and a reduced diameter portion 43*d* for pressing the insulators 44*a* to 44*c* and the powder compacts 45*a* and 45*b* in a downward direction in FIG. 1 through the metal ring 46.

The insulators 44*a* to 44*c* and the powder compacts 45*a* and 45*b* are disposed between the inner circumferential surface of the cylindrical member 41 and the sensor element 20. The insulators 44*a* to 44*c* serve as supporters for the powder compacts 45*a* and 45*b*. Examples of the material of the insulators 44*a* to 44*c* include ceramics such as alumina, steatite, zirconia, spinel, cordierite, and mullite and glass. The powder compacts 45*a* and 45*b* are formed, for example, by molding a powder and each serve as a sealing medium. Examples of the material of the powder compacts 45*a* and 45*b* include talc and ceramic powders such as alumina powder and boron nitride powder, and the powder compacts 45*a* and 45*b* may each contain at least one of these materials. The powder compact 45*a* is filled between the insulators 44*a* and 44*b*, sandwiched therebetween from opposite sides (forward and rear sides) in the axial direction, and pressed by the insulators 44*a* and 44*b*. The powder compact 45*b* is filled between the insulators 44*b* and 44*c*, sandwiched therebetween from opposite sides (forward and rear sides) in the axial direction, and pressed by the insulators 44*b* and 44*c*. The insulators 44*a* to 44*c* and the powder compacts 45*a* and 45*b* are sandwiched between the bottom surface 42*b* of the thick-walled portion 42*a* of the main metal fitting 42 and both the reduced diameter portion 43*d* and the metal ring 46 and pressed from the forward and rear sides. The pressing force applied by the reduced diameter portions 43*c* and 43*d* causes the powder compacts 45*a* and 45*b* to be compressed between the cylindrical member 41 and the sensor element 20, and the powder compacts 45*a* and 45*b* close the communication between the element chamber 33 in the protective cover 30 and a space 49 in the external cylinder 48 and fix the sensor element 20.

The bolt 47 is fixed to the outer side of the main metal fitting 42 so as to be coaxial with the main metal fitting 42. The bolt 47 has a male thread portion formed on the outer circumferential surface of the bolt 47. The male thread portion is inserted into a fixing member 59 that is welded to the pipe 58 and has a female thread portion formed on the inner circumferential surface of the fixing member 59. In this manner, the gas sensor 10 can be fixed to the pipe 58 with the forward end side of the sensor element 20 of the gas sensor 10 and the protective cover 30 protruding into the pipe 58.

The external cylinder 48 is a cylindrical metallic member and covers the inner cylinder 43, the rear end side of the sensor element 20, and the connector 50. An upper portion of the main metal fitting 42 is inserted into the external cylinder 48. The lower end of the external cylinder 48 is welded to the main metal fitting 42. The plurality of lead wires 55 connected to the connector 50 are drawn from the upper end of the external cylinder 48 to the outside. The connector 50 is in contact with and electrically connected to upper connector electrodes 71 and lower connector electrodes 72 that are disposed on rear end portions of respective surfaces of the sensor element 20. The lead wires 55 are electrically continuous with electrodes 64 to 68 and a heater 69 of the sensor element 20 through the connector 50. The gap between the external cylinder 48 and the lead wires 55 is sealed by the rubber stopper 57. The space 49 inside the external cylinder 48 is filled with a reference gas. A sixth surface 60*f* (rear end surface) of the sensor element 20 is disposed inside the space 49.

As shown in FIGS. 2 to 7, the sensor element 20 includes the element body 60, a detection portion 63, the heater 69, the upper connector electrodes 71, the lower connector electrodes 72, a protective layer 80, a first dense layer 92, a second dense layer 95, and the intermediate layer 98. The element body 60 includes a layered body prepared by stacking a plurality of oxygen-ion-conductive solid electrolyte layers. As shown in FIG. 3, in the present embodiment, the element body 60 includes six solid electrolyte layers 78*a* to 78*f*. The solid electrolyte layers 78*a* to 78*f* are made of a ceramic containing zirconia ($ZrO_2$) as a main component. The element body 60 has an elongate rectangular parallelepiped shape whose longitudinal direction extends in the forward-rearward direction and has first to sixth surfaces 60*a* to 60*f* that are the upper, lower, left, right, forward, and rear outer surfaces of the element body 60. The first to fourth surfaces 60*a* to 60*d* are surfaces extending in the longitudinal direction of the element main body 60 and correspond to the side surfaces of the element main body 60. The fifth surface 60*e* is the forward end surface of the element body 60, and the sixth surface 60*f* is the rear end surface of the element body 60. As for the dimensions of the element body 60, for example, the length may be from 25 mm to 100 mm inclusive. The width may be from 2 mm to 10 mm inclusive, and the thickness may be from 0.5 mm to 5 mm inclusive. The element body 60 has formed therein: a measurement-object gas inlet 61 having an opening on the fifth surface 60*e* to introduce the measurement-object gas into the element body 60; and a reference gas inlet 62 having an opening on the sixth surface 60*f* to introduce the reference gas (air in the present embodiment) used as a reference for detection of the specific gas concentration into the element body 60.

The detection portion 63 is used to detect the specific gas concentration in the measurement-object gas. The detection portion 63 includes a plurality of electrodes disposed on a forward end side of the element body 60. In the present embodiment, the detection portion 63 includes an outer electrode 64 disposed on the first surface 60*a* and further includes an inner main pump electrode 65, an inner auxiliary pump electrode 66, a measurement electrode 67, and a reference electrode 68 that are disposed inside the element body 60. The inner main pump electrode 65 and the inner auxiliary pump electrode 66 are disposed on the inner circumferential surface of an internal space of the element body 60 and each have a tunnel-like structure.

The principle of the detection of the specific gas concentration in the measurement-object gas by the detection portion 63 is well known, and its detailed description will be omitted. The detection portion 63 detects the specific gas concentration, for example, in the following manner. The detection portion 63 pumps oxygen in the measurement-object gas around the inner main pump electrode 65 to the outside (the element chamber 33) or pumps oxygen from the outside according to a voltage applied between the outer electrode 64 and the inner main pump electrode 65. Moreover, the detection portion 63 pumps oxygen in the measurement-object gas around the inner auxiliary pump electrode 66 to the outside (the element chamber 33) or pumps oxygen from the outside according to a voltage applied between the outer electrode 64 and the inner auxiliary pump electrode 66. This allows the measurement-object gas whose oxygen concentration has been adjusted to a prescribed value to reach the measurement electrode 67. The measurement electrode 67 functions as a NOx reduction catalyst and reduces the specific gas (NOx) in the measurement-object gas that has reached the measurement electrode 67. Then the detection portion 63 generates an electric signal corresponding to an electromotive force generated between the measurement electrode 67 and the reference electrode 68 according to the oxygen concentration in the reduced gas or corresponding to a current flowing between the measurement electrode 67 and the outer electrode 64 according to the electromotive force. The electric signal generated by the detection portion 63 is a signal indicating a value corresponding to the specific gas concentration in the measurement-object gas (a value from which the specific gas concentration can be derived) and corresponds to the detection value detected by the detection portion 63.

The heater 69 is an electric resistor disposed inside the element body 60. When electric power is supplied to the heater 69 from the outside, the heater 69 generates heat and heats the element body 60. The heater 69 can heat the solid electrolyte layers 78*a* to 78*f* included in the element body 60, can keep them hot, and can adjust their temperature to the temperature at which the solid electrolyte layers 78*a* to 78*f* are activated (e.g., 800° C.)

The upper connector electrodes 71 and the lower connector electrodes 72 are disposed on rear end-side portions of side surfaces of the element body 60 and are electrodes that allow electrical continuity between the element body 60 and the outside. The upper and lower connector electrodes 71 and 72 are not covered with the protective layer 80 and are exposed. In the present embodiment, the upper connector electrodes 71 include four upper connector electrodes 71*a* to 71*d* arranged in the left-right direction and disposed on the rear end side of the first surface 60*a*. The lower connector electrodes 72 include four lower connector electrodes 72*a* to 72*d* arranged in the left-right direction and disposed on the rear end side of the second surface 60*b* (lower surface) opposite to the first surface 60*a* (upper surface). Each of the connector electrodes 71*a* to 71*d* and 72*a* to 72*d* is electrically continuous with a corresponding one of the heater 69 and the plurality of electrodes 64 to 68 of the detection portion 63. In the present embodiment, the upper connector electrode 71*a* is electrically continuous with the measurement electrode 67, and the upper connector electrode 71*b* is electrically continuous with the outer electrode 64. The upper connector electrode 71*c* is electrically continuous with the inner auxiliary pump electrode 66, and the upper connector electrode 71*d* is electrically continuous with the inner main pump electrode 65. The lower connector electrodes 72*a* to 72*c* are electrically continuous with the heater 69, and the lower connector electrode 72*d* is electrically continuous with the reference electrode 68. The upper connector electrode 71*b* is electrically continuous with the outer electrode 64 through an outer lead wire 75 disposed on the first surface 60*a* (see FIGS. 3 and 4). Each of the other connector electrodes is electrically continuous with a corresponding electrode or the heater 69 through a lead wire disposed inside the element body 60, a through hole, etc.

The outer lead wire 75 is a conductor containing a noble metal such as platinum (Pt) or a high-melting point metal such as tungsten (W) or molybdenum (Mo). Preferably, the outer lead wire 75 is a cermet conductor containing a noble metal or a high-melting point metal and the oxygen-ion-conductive solid electrolyte contained in the element body 60 (zirconia in the present embodiment). In the present embodiment, the outer lead wire 75 is a cermet conductor containing platinum and zirconia. The porosity of the outer lead wire 75 may be, for example, from 5% to 40% inclusive. The line width of the outer lead wire 75 (its thickness, i.e., the width in the left-right direction) is, for example, from 0.1 mm to 1.0 mm inclusive. An unillustrated insulating layer for insulation between the outer lead wire 75 and the solid electrolyte layer 78*a* of the element body 60 may be disposed between the outer lead wire 75 and the first surface 60*a* of the element body 60.

The protective layer 80 includes inner porous layers 81 and an outer porous layer 85. The inner porous layers 81 are porous bodies that cover at least the forward end side of the side surfaces of the element body 60 on which the upper and lower connector electrodes 71 and 72 are disposed, i.e., of the first and second surfaces 60*a* and 60*b*. In the present embodiment, the inner porous layers 81 cover the first and second surfaces 60*a* and 60*b*. The outer porous layer 85 is a porous body that covers the forward end side of the element body 60. The outer porous layer 85 is disposed on the outer side of the inner porous layers 81.

The inner porous layers 81 include a first inner porous layer 83 that covers the first surface 60*a* and a second inner porous layer 84 that covers the second surface 60*b*. The first inner porous layer 83 covers the entire region, from the forward end to the rear end, of the first surface 60*a* on which the upper connector electrodes 71*a* to 71*d* are disposed, except for the regions in which the first dense layer 92 and the upper connector electrodes 71 are present (see FIGS. 2 to 4). The width of the first inner porous layer 83 in the left-right direction is the same as the width of the first surface 60*a* in the left-right direction, and the first inner porous layer 83 covers the first surface 60*a* so as to extend from the left edge of the first surface 60*a* to its right edge. Since the first dense layer 92 is present, the first inner porous layer 83 is divided in the longitudinal direction into a forward end-side portion 83*a* located forward of the first dense layer 92 and a rear end-side portion 83*b* located rearward of the first dense layer 92. The first inner porous layer 83 covers at least partially the outer electrode 64 and the outer lead wire 75. In the present embodiment, as shown in FIGS. 3 and 4, the first inner porous layer 83 covers the entire outer electrode 64 and covers the entire portion of the outer lead wire 75 in which the first dense layer 92 is not present. The first inner porous layer 83 protects the outer electrode 64 and the outer lead wire 75 from components of the measurement-object gas such as sulfuric acid and plays a role in preventing corrosion of the outer electrode 64 and the outer lead wire 75.

The second inner porous layer 84 covers the entire region, from the forward end to the rear end, of the second surface 60*b* on which the lower connector electrodes 72*a* to 72*d* are disposed, except for the regions in which the second dense layer 95 and the lower connector electrodes 72 are present (see FIGS. 2, 3, and 5). The width of the second inner porous layer 84 in the left-right direction is the same as the width of the second surface 60*b* in the left-right direction, and the second inner porous layer 84 covers the second surface 60*b* so as to extend from the left edge of the second surface 60*b* to its right edge. The presence of the second dense layer 95 divides the second inner porous layer 84 into a forward end-side portion 84*a* located forward of the second dense layer 95 in the longitudinal direction and a rear end-side portion 84*b* located rearward of the second dense layer 95.

The outer porous layer 85 covers the first to fifth surfaces 60*a* to 60*e*. The outer porous layer 85 covers the inner porous layers 81 to thereby cover the first surface 60*a* and the second surface 60*b*. The length of the outer porous layer 85 in the forward-rearward direction is shorter than that of the inner porous layers 81. Unlike the inner porous layers 81, the outer porous layer 85 covers only the forward end of the element body 60 and a region around the forward end. In this case, the outer porous layer 85 covers a portion of the element body 60 that surrounds the electrodes 64 to 68 of the detection portion 63, i.e., a portion of the element body 60 that is disposed inside the element chamber 33 and exposed to the measurement-object gas. In this manner, the outer porous layer 85 plays a role in preventing the occurrence of cracking in the element body 60 that are caused by adhesion of, for example, moisture etc. in the measurement-object gas.

The protective layer 80 is formed of, for example, a ceramic porous material such as an alumina porous material, a zirconia porous material, a spinel porous material, a cordierite porous material, a titania porous material, or a magnesia porous material. In the present embodiment, the protective layer 80 is formed of an alumina porous material. The thickness of the first inner porous layer 83 and the thickness of the second inner porous layer 84 may be, for example, 5 μm or more and may be 14 μm or more. The thickness of the first inner porous layer 83 and the thickness of the second inner porous layer 84 may be 40 μm or less and may be 23 μm or less. The thickness of the outer porous layer 85 is, for example, from 40 μm to 800 μm inclusive. The porosity of the protective layer 80 is 10% or more. The protective layer 80 covers the outer electrode 64 and the measurement-object gas inlet 61. However, when the porosity is 10% or more, the measurement-object gas can pass through the protective layer 80. The porosity of the inner porous layers 81 may be from 10% to 50% inclusive. The porosity of the outer porous layer 85 may be from 10% to 85% inclusive. The porosity of the outer porous layer 85 may be higher than the porosity of the inner porous layers 81.

The porosity of the inner porous layers 81 is a value derived as follows using an image (SEM image) obtained by observation using a scanning electron microscope (SEM). First, the sensor element 20 is cut in the thickness direction of the inner porous layers 81, and a cross section of one of the inner porous layers 81 is used as an observation surface. The cross-section is embedded in a resin and polished to obtain an observation sample. Next, the magnification of the SEM is set to 1000× to 10000×, and an image of the observation surface of the observation sample is captured to thereby obtain an SEM image of the inner porous layer 81. Next, the image obtained is subjected to image analysis, and a threshold value is determined by a discriminant analysis method (Otsu's binarization) using a brightness distribution obtained from the brightness data of pixels in the image. Using the determined threshold value, the pixels in the image are binarized and classified into object portions and pore portions, and the area of the object portions and the area of the pore portions are computed. Then the ratio of the area of the pore portions to the total area (the total area of the object portions and the pore portions) is computed as a porosity (unit: %). The porosity of the outer porous layer 85 and the porosities of the first dense layer 92, the second dense layer 95, and the intermediate layer 98 described later are computed in the same manner as described above.

The first dense layer 92 and the second dense layer 95 serve as water intrusion preventing portions that prevent capillary action of water in the longitudinal direction of the element body 60. The first dense layer 92 is disposed on the first surface 60a on which the upper connector electrodes 71 and the first inner porous layer 83 are disposed. The first dense layer 92 is disposed on the first surface 60a so as to divide the first inner porous layer 83 into forward and rear portions in the longitudinal direction as described above.

The first dense layer 92 is disposed closer to the forward end of the element body 60 than the upper connector electrodes 71, i.e., disposed forward of the upper connector electrodes 71. The first dense layer 92 is disposed rearward of the outer electrode 64. The first dense layer 92 is disposed rearward of all the plurality of electrodes 64 to 68, including the outer electrode 64, included in the detection portion 63 (see FIG. 3). The first dense layer 92 is disposed at a position that overlaps the insulator 44b in the forward-rearward direction (see FIG. 1). In other words, a region extending from the forward end of the first dense layer 92 to its rear end is located within a region extending from the forward end of the insulator 44b to its rear end. The first dense layer 92 plays a role in preventing moisture moved rearward through the forward end-side portion 83a by capillary action from passing through the first dense layer 92 to thereby prevent the moisture from reaching the upper connector electrodes 71. The first dense layer 92 is a dense layer with a porosity of less than 10%. The width of the first dense layer 92 in the left-right direction is the same as the width of the first surface 60a in the left-right direction, and the first dense layer 92 covers the first surface 60a so as to extend from the left edge of the first surface 60a to its right edge. The first dense layer 92 is adjacent to the rear end of the forward end-side portion 83a. The first dense layer 92 is adjacent to the forward end of the rear end-side portion 83b. As shown in FIG. 4, the first dense layer 92 covers part of the outer lead wire 75.

The second dense layer 95 is disposed on the second surface 60b on which the lower connector electrodes 72 and the second inner porous layer 84 are disposed. The second dense layer 95 is disposed on the second surface 60b so as to divide the second inner porous layer 84 into forward and rear portions in the longitudinal direction as described above. The second dense layer 95 is disposed closer to the forward end of the element body 60 than the lower connector electrodes 72, i.e., disposed forward of the lower connector electrodes 72. The second dense layer 95 is disposed rearward of the outer electrode 64. The second dense layer 95 is disposed rearward of all the plurality of electrodes 64 to 68, including the outer electrode 64, included in the detection portion 63 (see FIG. 3). The second dense layer 95 is disposed at a position that overlaps the insulator 44b in the forward-rearward direction (see FIG. 1). In other words, a region extending from the forward end of the second dense layer 95 to its rear end is located within a region extending from the forward end of the insulator 44b to its rear end. The second dense layer 95 plays a role in preventing moisture moved rearward through the forward end-side portion 84a by capillary action from passing through the second dense layer 95 to thereby prevent the moisture from reaching the lower connector electrodes 72. The second dense layer 95 is a dense layer with a porosity of less than 10%. The width of the second dense layer 95 in the left-right direction is the same as the width of the second surface 60b in the left-right direction, and the second dense layer 95 covers the second surface 60b so as to extend from the left edge of the second surface 60b to its right edge. The second dense layer 95 is adjacent to the rear end of the forward end-side portion 84a. The second dense layer 95 is adjacent to the forward end of the rear end-side portion 84b.

The length Le of each of the first dense layer 92 and the second dense layer 95 in the longitudinal direction (see FIGS. 4 and 5) is preferably 0.5 mm or more. When the length Le is 0.5 mm or more, the passage of moisture through the first dense layer 92 and the second dense layer 95 can be prevented sufficiently. The length Le may be 5 mm or more. The length Le may be 25 mm or less and may be 20 mm or less. In the present embodiment, the length Le of the first dense layer 92 and the length Le of the second dense layer 95 are the same but may be different values.

The first dense layer 92 and the second dense layer 95 differ from the protective layer 80 in that their porosity is less than 10%. However, a ceramic composed of any of the materials exemplified for the protective layer 80 described above can be used. Specifically, the first dense layer 92 may be a ceramic porous body containing, as a main component, at least one type of ceramic particles selected from alumina particles, zirconia particles, spinel particles, cordierite particles, titania particles, and magnesia particles. In the present embodiment, the first dense layer 92 and the second dense layer 95 are both formed of a ceramic containing alumina as a main component. The thickness of the first dense layer 92 and the thickness of the second dense layer 95 may each be, for example, from 1 µm to 40 µm inclusive. The thickness of the first dense layer 92 and the thickness of the second dense layer 95 may each be 20 µm or less, may be 9 µm or less, and may be 3 µm or less. The porosity of the first dense layer 92 and the porosity of the second dense layer 95 are each preferably 8% or less and more preferably 5% or less. The smaller the porosity, the further the first dense layer 92 and the second dense layer 95 can reduce the capillary action of water in the longitudinal direction of the element body 60.

As shown in FIGS. 1 to 3, 6, and 7, the intermediate layer 98 is disposed between the first dense layer 92 and the element body 60. Although the details will be described later, the intermediate layer 98 plays a role in reducing the occurrence of cracking in the sensor element 20. As shown in FIG. 7, the intermediate layer 98 is located between the first dense layer 92 and the outer lead wire 75 and covers the outer lead wire 75. Therefore, the first dense layer 92 covers the outer lead wire 75 with the intermediate layer 98 interposed therebetween. As shown in FIG. 6, in the present embodiment, the length of the intermediate layer 98 in the forward-rearward direction is the same as the length Le of the first dense layer 92. Specifically, the intermediate layer 98 is disposed only on the lower side of the first dense layer 92 and not disposed between the first inner porous layer 83 and the element body 60. As shown in FIG. 7, the width of the intermediate layer 98 in the left-right direction is the same as the width of the first surface 60a in the left-right direction. Moreover, the width of the intermediate layer 98 in the left-right direction is the same as the width of the first dense layer 92 in the left-right direction. The thickness T of the intermediate layer 98 is, for example, from 1 µm to 40 µm inclusive. Like the inner porous layer 81, the intermediate layer 98 may have a porosity of 10% or more, i.e., may be a porous body. The porosity of the intermediate layer 98 may be 50% or less. Like the first dense layer 92, the intermediate layer 98 may have a porosity of less than 10%, i.e., may be dense. The porosity of the intermediate layer 98 may be 8% or less and may be 5% or less. In the present embodiment, the intermediate layer 98 is dense. When the thickness T of the intermediate layer 98 is 1 µm or more, the effect of the presence of the intermediate layer 98 in reducing the occurrence of cracking in the sensor element 20 can be obtained more reliably. The thickness T of the intermediate layer 98 may be 10 µm or less.

The thickness T of the intermediate layer 98 may be the thickness T1 of the thinnest portion of the intermediate layer 98 (for example, a portion located directly above the outer lead wire 75 as shown in FIG. 7) or the overall average thickness T2 of the intermediate layer 98. Even when the thickness T used is the thickness T1 or the thickness T2, the effect of reducing the occurrence of cracking can be obtained more reliably when the thickness T is 1 µm or more.

The intermediate layer 98 may be formed, for example, of a ceramic containing, as a main component, at least one type of ceramic particles selected from alumina particles, zirconia particles, spinel particles, cordierite particles, titania particles, and magnesia particles. The intermediate layer 98 may be formed of a noble metal such as platinum. The intermediate layer 98 may be formed of cermet containing the above-described ceramic particles and noble metal particles. Preferably, the intermediate layer 98 contains, as main components, the main component of the solid electrolyte layers 78a to 78f and the main component of the first dense layer 92. In the present embodiment, the intermediate layer 98 is a ceramic containing, as main components, zirconia used as the main component of the solid electrolyte layers 78a to 78f and alumina used as the main component of the first dense layer 92.

A method for producing the gas sensor 10 having the above-described structure will be described below. First a method for producing the sensor element 20 will be described. The method for producing the sensor element 20 includes a production step of producing a green sensor element that is the sensor element 20 before firing and a firing step of firing the green sensor element. In the present embodiment, the outer porous layer 85 is formed by plasma spraying after the firing step. Therefore, the green sensor element produced in the production step does not include a green outer porous layer 85, and the sensor element 20 after the firing step does not include the outer porous layer 85.

[Production Step]

In the production step, the green sensor element that is the sensor element 20 before firing is produced. In the production step, first, six ceramic green sheets (green solid electrolyte layers) corresponding to the solid electrolyte layers 78a to 78f included in the element body 60 are prepared. The ceramic green sheets are produced, for example, by mixing a solvent, a binder, etc. with a raw material powder containing the material of the solid electrolyte layers 78a to 78f (a zirconia powder in the present embodiment) to obtain a paste containing the material of the raw material powder as a main component and then forming the paste into a sheet shape. If necessary, through holes, grooves, etc. are punched in the ceramic green sheets to form portions that later become inner spaces of the element body 60 through firing. Next, patterns for green electrodes, green lead wires, green connector electrodes, a green heater, etc. are formed by screen printing on the ceramic green sheets to be used as the solid electrolyte layers 78a to 78f. The green electrodes later become the above-described electrodes 64 to 68 of the detection portion 63 through firing. The green lead wires later become, through firing, the lead wires that connect the electrodes to the upper connector electrodes 71 and the lower connector electrodes 72. The green lead wires include a lead wire that later becomes the outer lead wire 75 through firing. The green connector electrodes later become the upper connector electrodes 71 and the lower connector electrodes 72 through firing. The green heater later becomes the heater 69 through firing. Moreover, patterns for a green intermediate layer that later becomes the intermediate layer 98 through firing, a green first dense layer that later becomes the first dense layer 92 through firing, and a green first inner porous layer that later becomes the first inner porous layer 83 through firing are formed by screen printing on a surface of the ceramic green sheet that later becomes the solid electrolyte layer 78a through firing (a surface that later becomes the first surface 60a of the element body 60).

Similarly, patterns for a green second dense layer that later becomes the second dense layer 95 through firing and a green second inner porous layer that later becomes the second inner porous layer 84 through firing are formed by screen printing on a surface of the ceramic green sheet that later becomes the solid electrolyte layer 78f through firing (a surface that later becomes the second surface 60b of the element body 60). Next, the six ceramic green sheets with the patterns formed thereon are stacked to form a layered body. The layered body is cut into small layer bodies having the same size as the size of the sensor element 20. These small layered bodies are green sensor elements. The patterns for the green first inner porous layer, the green second inner porous layer, the green intermediate layer, the green first dense layer, and the green second dense layer may be printed after the production of the layered body described above.

The paste used to form the green first inner porous layer is, for example, a paste that is prepared by mixing a raw material powder composed of the material of the above-described first inner porous layer 83 (an aluminum powder in the present embodiment), a binder, a solvent, a pore-forming material, etc. and that contains, as a main component, the material of the raw material powder. The paste forming the green second inner porous layer is prepared in the same manner as described above. The paste used to form the green first dense layer is, for example, a paste that is prepared by mixing a raw material powder composed of the material of the above-described first dense layer 92 (an aluminum powder in the present embodiment), a binder, a solvent, etc. and that contains, as a main component, the material of the raw material powder. To control the porosity of the first dense layer 92, a pore-forming material may be added to the paste. The paste for forming the green second dense layer is prepared in the same manner as above. The paste used to form the green intermediate layer is, for example, a paste that is prepared by mixing a raw material powder composed of the materials of the above-described intermediate layer 98 (an aluminum powder and a zirconia powder in the present embodiment), a binder, a solvent, etc. and that contains, as main components, the materials of the raw material powder. To control the porosity of the intermediate layer 98, a pore-forming material may be added to the paste.

The green first inner porous layer and the green second inner porous layer may be formed using the same paste or using pastes prepared using different raw material powders. The green first dense layer and the green second dense layer may also be formed using the same paste or using pastes prepared using different raw material powders.

[Firing Step]

Next, the firing step of firing the green sensor element obtained in the production step is performed. In the firing step, the green sensor element is fired at a prescribed firing temperature (e.g., 1360° C.±50° C.), and then the temperature is lowered to room temperature (e.g., 20° C.) after firing. In this manner, the six ceramic green sheets become the solid electrolyte layers 78a to 78f, and the green electrodes become the electrodes 64 to 68. The green lead wires become the plurality of wires including the outer lead wire 75, and the green connector electrodes become the upper connector electrodes 71 and the lower connector electrodes 72. Moreover, the green heater becomes the heater 69. The green intermediate layer becomes the intermediate layer 98, and the green first dense layer becomes the first dense layer 92. The green first inner porous layer becomes the first inner porous layer 83, and the green second dense layer becomes the second dense layer 95. The green second inner porous layer becomes the second inner porous layer 84. The sensor element 20 is obtained through the firing step.

In the present embodiment, after the firing step has been performed to produce the sensor element 20, the outer porous layer 85 is formed by plasma spraying. The plasma spraying can be performed, for example, in the same manner as in plasma spraying described in Japanese Unexamined Patent Application Publication No. 2016-109685. Then the gas sensor 10 equipped with the sensor element 20 is produced. First, the sensor element 20 is caused to pierce axially through the cylindrical member 41, and the insulator 44a, the powder compact 45a, the insulator 44b, the powder compact 45b, the insulator 44c, and the metal ring 46 are placed in this order between the inner circumferential surface of the cylindrical member 41 and the sensor element 20. Next, the metal ring 46 is pressed to compress the powder compacts 45a and 45b. With this state maintained, the reduced diameter portions 43c and 43d are formed to thereby produce the element-sealing member 40, and the gap between the inner circumferential surface of the cylindrical member 41 and the sensor element 20 is thereby sealed. Then the protective cover 30 is welded to the element-sealing member 40, and the bolt 47 is attached to obtain the assembly 15. Then the lead wires 55 piercing through the rubber stopper 57 and the connector 50 connected to the lead wires 55 are prepared, and the connector 50 is connected to the rear end side of the sensor element 20. Then the external cylinder 48 is welded and fixed to the main metal fitting 42 to thereby obtain the gas sensor 10.

In the sensor element 20 in the present embodiment, when the thermal expansion coefficients of the solid electrolyte layers 78a to 78f, the first dense layer 92, and the intermediate layer 98 in the temperature range of from 20° C. to 1360° C. are denoted by thermal expansion coefficients Ea, Eb, and Ec, respectively, the ratio Ea/Eb is more than 1.0 and 5.0 or less, and the relation Ea>Ec>Eb is satisfied. The thermal expansion coefficients Ea to Ec are not volume expansion coefficients but are linear expansion coefficients. Let the median of the thermal expansion coefficient Ea and the thermal expansion coefficient Eb be Ed (=(Ea+Eb)/2). Then it is preferable that the thermal expansion coefficient Ec satisfies formula (1) below. The thermal expansion coefficients Ea, Eb, and Ec are referred to also as thermal expansion coefficients A', B', and C'. The median Ed is referred to also as the median D'.

$$Ed-0.8\times(Ed-Eb)<Ec<Ed+0.8\times(Ea-Ed) \tag{1}$$

The thermal expansion coefficient Ea of the solid electrolyte layers 78a to 78f is measured by thermomechanical analysis (TMA) as follows. First, the sensor element 20 is cut such that a portion including the solid electrolyte layers 78a to 78f of the element body 60 is cut out to thereby obtain a measurement piece. Next, the measurement piece is placed in a container, and the expansion coefficient of the measurement piece when the temperature is changed from 20° C. to 1360° C. is measured under an applied load of 1 g. Specifically, a dimension a1' of the measurement piece at 20° C. is measured. Next, a dimension a2' of the measurement piece heated to 1360° C. while a load of 1 g is applied is measured. Then the thermal expansion coefficient Ea is computed using the formula: the thermal expansion coefficient Ea[%]=(a2'−a1')/a1'×100. The dimensions a1' and a2' of the measurement piece are measured as dimensions in the forward-rearward direction, i.e., the longitudinal direction, of the sensor element 20. Similarly, the thermal expansion coefficient Eb is computed using a measurement piece that is cut from the sensor element 20 so as to include part of the first dense layer 92, and the thermal expansion coefficient Ec is computed using a measurement piece that is cut from the sensor element 20 so as to include part of the intermediate layer 98. When thermal expansion coefficients of the solid electrolyte layers 78a to 78f are not the same, e.g., when the materials of the solid electrolyte layers 78a to 78f are not the same, the thermal expansion coefficient of a layer closest to the first dense layer 92 and the intermediate layer 98 (the solid electrolyte layer 78a in the present embodiment) is used as the thermal expansion coefficient Ea.

The thermal expansion coefficients Ea to Ec of the sensor element 20 can be controlled as follows. For example, the thermal expansion coefficient Ea of the solid electrolyte layers 78a to 78f can be controlled by changing the material of the raw material powder contained in the paste for forming the ceramic green sheets. The thermal expansion coefficient Eb of the first dense layer 92 can be controlled by chaining the material of the raw material powder contained in the paste for forming the green first dense layer. The thermal expansion coefficient Ec of the intermediate layer 98 can be controlled by changing the material of the raw material powder contained in the paste for forming the green intermediate layer. Therefore, the ratio Ea/Eb can be set to be more than 1.0 and 5.0 or less by selecting an appropriate combination of the material of the raw material powder of the solid electrolyte layers 78a to 78f and the material of the raw material powder of the first dense layer 92. For example, the thermal expansion coefficient of zirconia at 40° C. to 400° C. is $10.5 \times 10^{-6}$/° C., and the thermal expansion coefficient of alumina at 40° C. to 400° C. is $7.2 \times 10^{-6}$/° C. Therefore, the thermal expansion coefficient of zirconia is larger than the thermal expansion coefficient of alumina. When the raw material powder of the solid electrolyte layers 78a to 78f is zirconia and the raw material powder of the first dense layer 92 is alumina, the thermal expansion coefficient Ea is larger than the thermal expansion coefficient Eb, and the ratio Ea/Eb can be set to be more than 1.0 and 5.0 or less. When cordierite (thermal expansion coefficient: less than $0.1 \times 10^{-6}$/° C.) or silicon nitride (thermal expansion coefficient: $2.8 \times 10^{-6}$/° C.), which are materials having a smaller thermal expansion coefficient than alumina, is used as the raw material powder of the first dense layer 92, the value of the ratio Ea/Eb can be larger than that when alumina is used (for example, a value of about 5.0) while the value of the ratio Ea/Eb is set to be more than 1.0 and 5.0 or less. When a material whose thermal expansion coefficient is between the thermal expansion coefficient of the material of the raw material powder of the solid electrolyte layers 78a to 78f and the thermal expansion coefficient of the material of the raw material powder of the first dense layer 92 is appropriately selected as the material of the raw material powder of the intermediate layer 98, Ea>Ec>Eb can be satisfied, and formula (1) can be satisfied. Alternatively, the raw material powder of the intermediate layer 98 may contain both the material of the raw material powder of the solid electrolyte layers 78a to 78f and the material of the raw material powder of the first dense layer 92. In this case also, Ea>Ec>Eb can be satisfied, and formula (1) can be satisfied. By appropriately controlling the volume ratio of the material of the raw material powder of the solid electrolyte layers 78a to 78f and the volume ratio of the material of the raw material powder of the first dense layer 92 in the raw material powder of the intermediate layer 98, the thermal expansion coefficient Ec can be controlled while Ea>Ec>Eb is satisfied, and this allows formula (1) to be satisfied.

Next, an example of the use of the thus-produced gas sensor 10 will be described below. When the measurement-object gas flows through the pipe 58 with the gas sensor 10 attached to the pipe 58 as shown in FIG. 1, the measurement-object gas flows through the protective cover 30 and into the element chamber 33, and the forward end side of the sensor element 20 is exposed to the measurement-object gas. Then, with the sensor element 20 heated by the heater 69, the measurement-object gas passes through the protective layer 80, reaches the outer electrode 64, and also reaches the sensor element 20 through the measurement-object gas inlet 61, and the detection portion 63 generates an electrical signal corresponding to the NOx concentration in the measurement-object gas as described above. By outputting this electrical signal through the upper and lower connector electrodes 71 and 72, the NOx concentration is detected based on the electrical signal.

In this case, the measurement-object gas may contain moisture, and the moisture may move through the protective layer 80 by capillary action. When the moisture reaches the exposed upper and lower connector electrodes 71 and 72, rust or corrosion may occur in the upper and lower connector electrodes 71 and 72 due to components such as water and sulfuric acid dissolved in water, or a short circuit may occur between adjacent ones of the upper and lower connector electrodes 71 and 72. However, in the present embodiment, even when moisture in the measurement-object gas moves through the protective layer 80 (in particular, the first inner porous layer 83 and the second inner porous layer 84) toward the rear end of the element body 60 by capillary action, the moisture reaches the first dense layer 92 or the second dense layer 95 before it reaches the upper and lower connector electrodes 71 and 72. Since the porosity of the first dense layer 92 is less than 10%, the capillary action of water in the longitudinal direction of the element body 60 is unlikely to occur. In this case, the first dense layer 92 can prevent moisture from passing through the first dense layer 92 from the forward end-side portion 83a side and reaching the upper connector electrodes 71 (the upper connector electrodes 71a to 71d). Therefore, in the sensor element 20, the occurrence of the above-described problem caused by water adhering to the upper connector electrodes 71 can be reduced. Similarly, the second dense layer 95 can prevent moisture from passing through the second dense layer 95 from the forward end-side portion 84a side and reaching the lower connector electrodes 72 (the lower connector electrodes 72a to 72d). Therefore, in the sensor element 20, the occurrence of the above-described problem caused by water adhering to the lower connector electrodes 72 is reduced. Preferably, the length Le of the first dense layer 92 in the longitudinal direction is 0.5 mm or more because the passage of moisture through the first dense layer 92 can be reduced sufficiently. Similarly, the length Le of the second dense layer 95 is 0.5 mm or more.

Moreover, the sensor element 20 has a ratio Ea/Eb of more than 1.0 and 5.0 or less and satisfies Ea>Ec>Eb as described above. Therefore, the intermediate layer 98 reduces the stress caused by the difference between the thermal expansion coefficient Ea of the solid electrolyte layers 78a to 78f and the thermal expansion coefficient Eb of the first dense layer 92 when the sensor element 20 is heated by the heater 69 during use. When stress is generated in the sensor element 20, cracking tends to occur. However, in the sensor element 20 in the present embodiment, the stress generated during heating is reduced, so that the occurrence of cracking in the sensor element 20 is reduced. Moreover, since formula (1) above is satisfied, the stress during heating of the sensor element 20 is further reduced, and the occurrence of cracking during heating of the sensor element 20 is further reduced. The ratio Ea/Eb is preferably 3.0 or less. When the ratio Ea/Eb is 3.0 or less, the thermal expansion coefficient Ea of the solid electrolyte layers 78a to 78f is closer to the thermal expansion coefficient Eb of the first dense layer 92, so that the occurrence of cracking in the sensor element 20 is further reduced.

When cracking occurs in the sensor element 20, particularly in the first dense layer 92 or the second dense layer 95, the function of the first dense layer 92 or the second dense layer 95 as the water intrusion preventing portion described above may deteriorate. However, since the occurrence of cracking in the sensor element 20 in the present embodiment is reduced, the function of the first dense layer 92 and the second dense layer 95 as the water intrusion preventing portions is unlikely to deteriorate, and thus the occurrence of the above-described problem caused by water adhering to the upper connector electrodes 71 and the lower connector electrodes 72 is reduced.

The correspondences between the components in the present embodiment and the components in the present invention will be clarified. The solid electrolyte layers 78a to 78f in the present embodiment correspond to the solid electrolyte layer in the present invention, and the element body 60 corresponds to the element body. The upper connector electrodes 71a to 71d correspond to the connector electrode, and the first surface 60a corresponds to the side surface on which the connector electrode is disposed. The first inner porous layer 83 corresponds to the porous layer, and the first dense layer 92 corresponds to the dense layer. The intermediate layer 98 corresponds to the intermediate layer. The detection portion 63 corresponds to the detection portion, and the outer lead wire 75 corresponds to the outer lead portion. The outer electrode 64 corresponds to the outer electrode.

In the gas sensor 10 in the present embodiment described above in detail, as for the thermal expansion coefficients Ea, Eb, and Ec of the solid electrolyte layers 78a to 78f, the first dense layer 92, and the intermediate layer 98 of the sensor element 20 in the temperature range of from 20° C. to 1360° C., the ratio Ea/Eb is more than 1.0 and 5.0 or less, and Ea>Ec>Eb is satisfied. In this case, the intermediate layer 98 reduces the stress caused by the difference between the thermal expansion coefficient Ea of the solid electrolyte layers 78a to 78f and the thermal expansion coefficient Eb of the first dense layer 92 when the sensor element 20 is heated during use. Therefore, the occurrence of cracking in the sensor element 20 during heating is reduced. Moreover, since the thermal expansion coefficients Ea to Ec in the sensor element 20 satisfy formula (1) above, the stress generated when the sensor element 20 is heated is reduced, and the occurrence of cracking is further reduced. Moreover, since the ratio Ea/Eb in the sensor element 20 is 3.0 or less, the occurrence of cracking is further reduced. In the sensor element 20, since the thickness T of the intermediate layer 98 is 1 μm or more, the above-described effect of the presence of the intermediate layer 98 in reducing the occurrence of cracking in the sensor element 20 is obtained more reliably.

The present invention is not limited to the embodiment described above. It will be appreciated that the present invention can be implemented in various forms so long as they fall within the technical scope of the invention.

Figure 8:
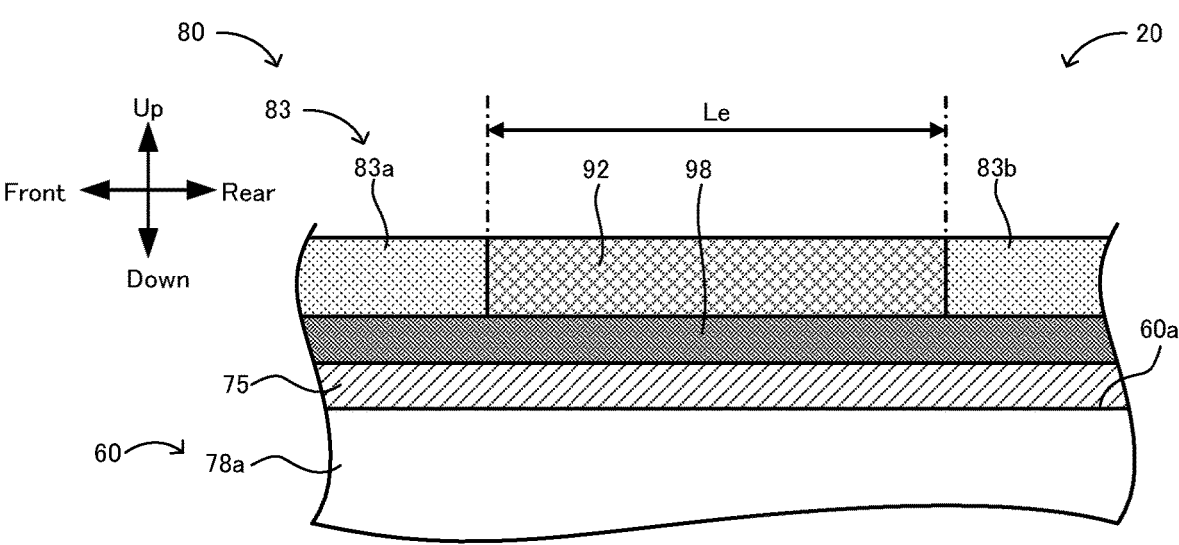
FIG. 8 is a partial cross-sectional view showing an intermediate layer 98 in a modification.

For example, in the above embodiment, the length of the intermediate layer 98 in the forward-rearward direction is the same as the length Le of the first dense layer 92 as shown in FIG. 6, but this is not a limitation. It is only necessary that the intermediate layer 98 be disposed at least between the first dense layer 92 and the element body 60. For example, as shown in FIG. 8, the length of the intermediate layer 98 may be larger than the length Le, and the intermediate layer 98 may be present also between the first inner porous layer 83 and the element body 60. In FIG. 8, the intermediate layer 98 extends frontward and rearward from the first dense layer 92. Specifically, the intermediate layer 98 is present between the forward end-side portion 83a and the element body 60 and also between the rear end-side portion 83b and the element body 60. The intermediate layer 98 may be present over a region extending from the forward end of the first surface 60a to its rear end. However, when the intermediate layer 98 is dense, it is preferable that the intermediate layer 98 is disposed so as to avoid overlapping the outer electrode 64 such that the intermediate layer 98 does not cover the outer electrode 64. The length of the intermediate layer 98 may be smaller than the length Le, and a region in which the intermediate layer 98 is not present may be present between the first dense layer 92 and the element body 60. In other words, it is only necessary that, in a cross-section taken in the forward-rearward direction, the intermediate layer 98 be present between at least part of the first dense layer 92 and the element body 60 (the solid electrolyte layer 78a). However, it is preferable that the intermediate layer 98 is present between the first dense layer 92 and the solid electrolyte layer 78a at least in a region extending from the forward end of the first dense layer 92 to its rear end, as shown in FIGS. 6 and 8. In this manner, the occurrence of cracking in the sensor element 20 can be further reduced. The length of the intermediate layer 98 in the forward-rearward direction may be, for example, from 0.5 mm to 55 mm inclusive.

Figure 9:
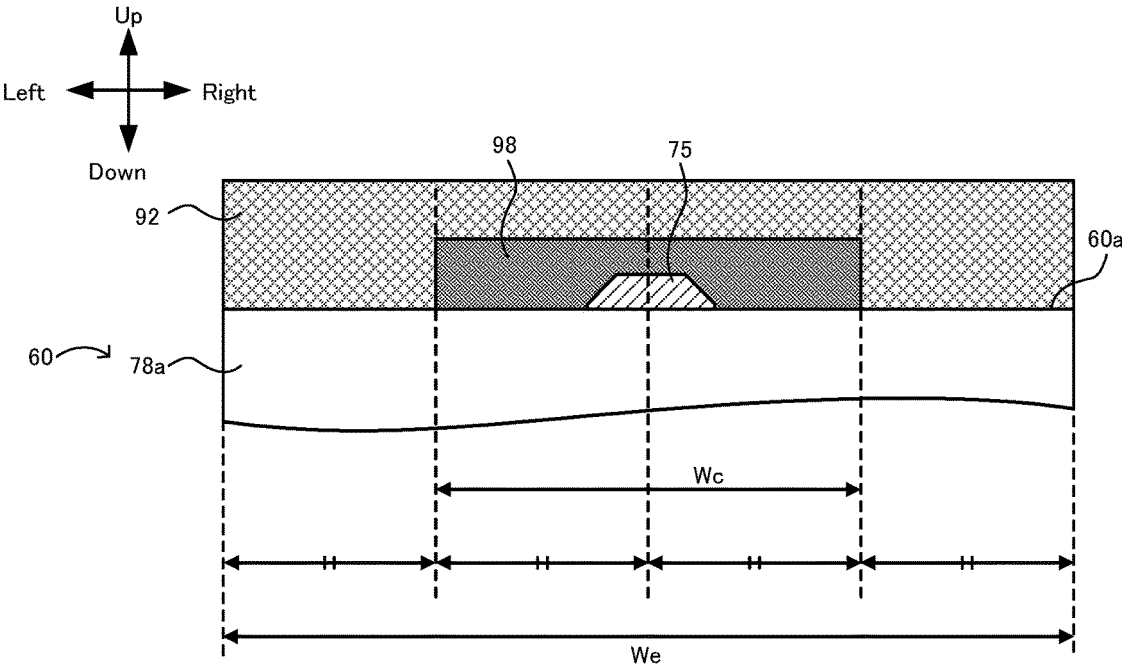
FIG. 9 is a partial cross-sectional view showing an intermediate layer 98 in a modification.
Figure 10:
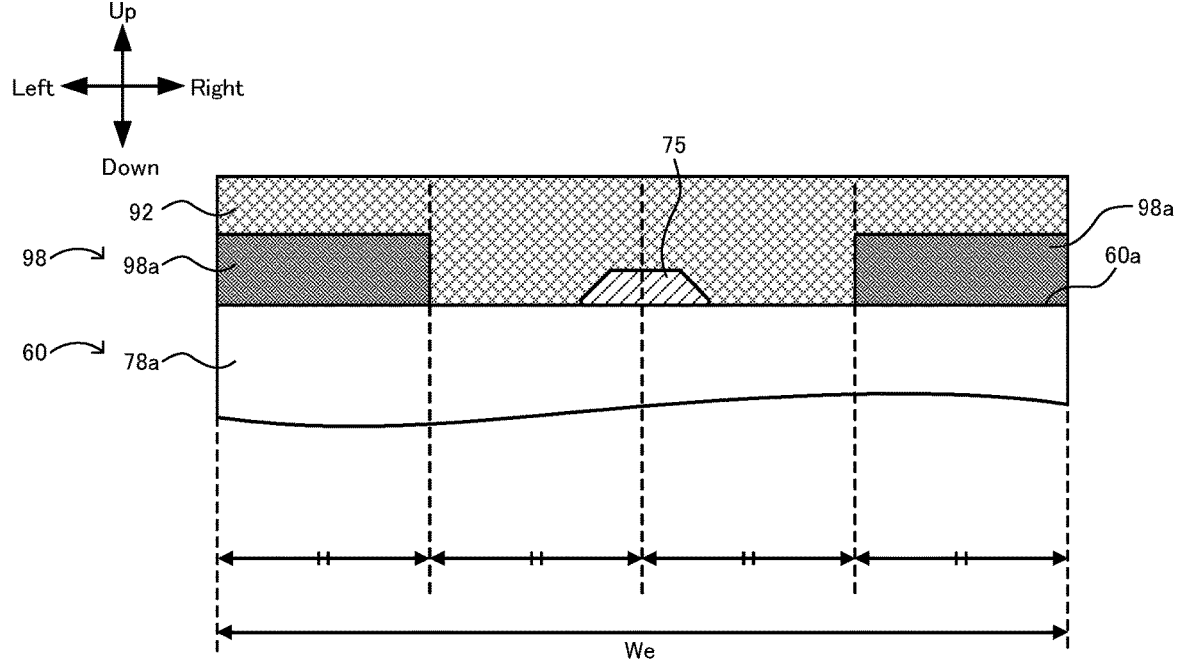
FIG. 10 is a partial cross-sectional view showing an intermediate layer 98 in a modification.

In the embodiment described above, as shown in FIG. 7, the width of the intermediate layer 98 in the left-right direction is the same as the width of the first surface 60a in the left-right direction and the width of the first dense layer 92 in the left-right direction, but this is not a limitation. It is only necessary that, in a cross section taken in the left-right direction, the intermediate layer 98 be present between at least part of the first dense layer 92 and the element body 60 (the solid electrolyte layer 78a), and the width of the intermediate layer 98 in the left-right direction may be smaller than that in FIG. 7. However, it is preferable that the intermediate layer 98 is present at least between the element body 60 and a region of the first dense layer 92 that is located at the center in the left-right direction and has a width of 50% (this region is hereinafter referred to as a central region). As shown in FIG. 9, the central region includes two left and right central regions among four regions obtained by dividing the left-right width We of the first dense layer 92 into quarters. It is preferable that the intermediate layer 98 is present at least between the central region of the first dense layer 92 and the element body 60, as shown in FIG. 9. In the cross section in the left-right direction in the example in FIG. 9, the intermediate layer 98 is present only between the central region of the first dense layer 92 and the element body 60, and the width Wc of the intermediate layer 98 in the left-right direction is the same as the width of the central region of the first dense layer 92 (We/2). Preferably, the width Wc of the intermediate layer 98 is equal to or larger than the width of the central region (We/2). As shown in FIG. 10, the intermediate layer 98 may be divided into left and right portions and may include an intermediate layer 98a located on the left side and an intermediate layer 98b located on the right side. In this case also, it is preferable that the width Wc of the intermediate layer 98 (the sum of the width of the intermediate layer 98a and the width of the intermediate layer 98b) is equal to or more than We/2. In FIG. 10, the sum of the width of the intermediate layer 98*a* and the width of the intermediate layer 98*b* is equal to We/2. From the viewpoint of reducing the occurrence of cracking in the sensor element 20 described above, the intermediate layer 98 in FIG. 9 that is present between the central region of the first dense layer 92 and the element body 60 is preferred to the intermediate layer 98 in FIG. 10.

Figure 11:
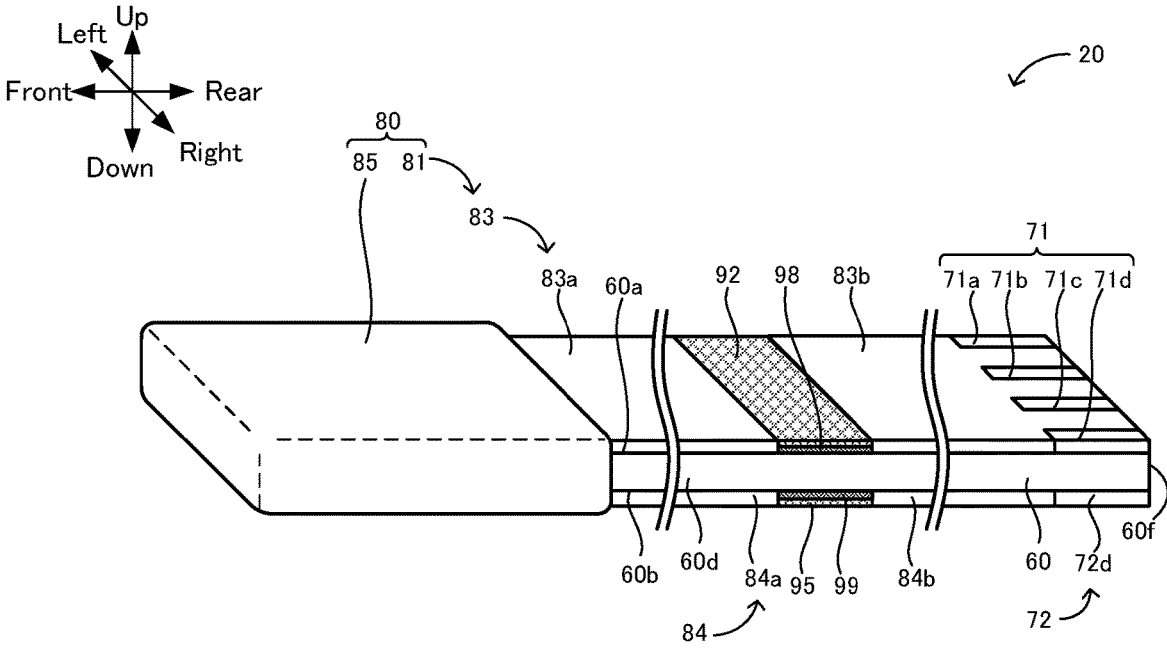
FIG. 11 is a perspective view of a sensor element 20 including an intermediate layer 99.

In the embodiment described above, the intermediate layer 98 is present between the element body 60 and the first dense layer 92 disposed on the first surface 60*a* side (the upper side) of the element body 60, but this is not a limitation. As shown in FIG. 11, an intermediate layer 99 may be present between the element body 60 and the second dense layer 95 disposed on the second surface 60*b* side (the lower side) of the element body 60. In this case, it is preferable that, when the thermal expansion coefficients of the solid electrolyte layers 78*a* to 78*f*, the second dense layer 95, and the intermediate layer 99 in the temperature range of from 20° C. to 1360° C. are denoted by thermal expansion coefficients Ea, Eb, and Ec, respectively, the ratio Ea/Eb is more than 1.0 and 5.0 or less and Ea>Ec>Eb is satisfied, and it is more preferable that formula (1) above is satisfied. The above-described various modes of the intermediate layer 98 can be applied to the intermediate layer 99. Preferably, the thermal expansion coefficient of the first dense layer 92 and the thermal expansion coefficient of the second dense layer 95 are the same, and the thermal expansion coefficient of the intermediate layer 98 and the thermal expansion coefficient of the intermediate layer 99 are the same.

Figure 12:
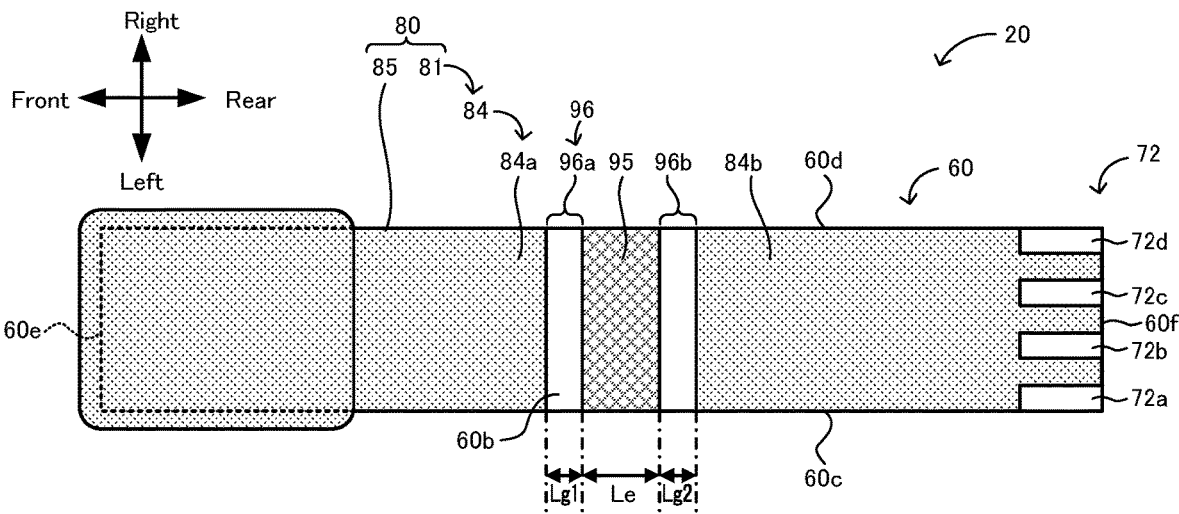
FIG. 12 is a bottom view showing a second dense layer 95 and gap regions 96 in a modification.

In the embodiment described above, the second surface 60*b* of the element body 60 may have an exposed portion on which the second inner porous layer 84 and the second dense layer 95 are not present. FIG. 12 shows an example in which gap regions 96 are disposed rearward and forward of the second dense layer 95 so as to be adjacent thereto. The gap regions 96 in FIG. 12 include a forward gap region 96*a* disposed between the forward end-side portion 84*a* and the second dense layer 95 and a rear gap region 96*b* disposed between the rear end-side portion 84*b* and the second dense layer 95. In portions in which the gap regions 96 are present, the second surface 60*b* is exposed. The gap regions 96 are spaces in which the second inner porous layer 84 is not present, so that the capillary action of water in the longitudinal direction of the element body 60 is unlikely to occur. Therefore, the gap regions 96 also serve as water intrusion preventing portions that prevent moisture moving in the longitudinal direction of the element body 60 from reaching the lower connector electrodes 72, as does the second dense layer 95. As for the gap regions 96, only one of the forward gap region 96*a* and the rear gap region 96*b* may be provided. The length Lg of the gap regions 96 in the longitudinal direction is preferably 1 mm or less. When the gap regions 96 include the forward gap region 96*a* and the rear gap region 96*b* as in FIG. 12, the length Lg is the sum of the length Lg1 of the forward gap region 96*a* in the longitudinal direction and the length Lg2 of the rear gap region 96*b* in the longitudinal direction. A gap region may be present on the first surface 60*a* side of the element body 60. However, in the embodiment described above, the outer lead wire 75 is disposed on the first surface 60*a*. It is therefore preferable, from the viewpoint of protecting the outer lead wire 75, that no gap region is present on the first surface 60*a* side.

In the embodiment described above, the outer porous layer 85 is formed by plasma spraying after the firing step, but this is not a limitation. For example, a green outer porous layer that later becomes the outer porous layer 85 through the firing step may be formed by, for example, dipping in the production step. In this case, the green outer porous layer becomes the outer porous layer 85 through the firing step. In the embodiment described above, the protective layer 80 may not include the outer porous layer 85.

In the embodiment described above, the first dense layer 92 divides the first inner porous layer 83 in the longitudinal direction into the forward end-side portion 83*a* and the rear end-side portion 83*b*, but this is not a limitation. The first dense layer 92 may be located rearward of the protective layer 80. For example, in the embodiment described above, the first inner porous layer 83 may not include the rear end-side portion 83*b*. Similarly, the second dense layer 95 may not divide the second inner porous layer 84 and may be located rearward of the protective layer 80. However, when the first inner porous layer 83 does not include the rear end-side portion 83*b*, part of the outer lead wire 75 is exposed. It is therefore preferable that the first inner porous layer 83 includes the rear end-side portion 83*b*.

In the embodiment described above, the first dense layer 92 and the second dense layer 95 are disposed at respective positions overlapping the insulator 44*b* in the forward-rearward direction, but this is not a limitation. For example, the first dense layer 92 and the second dense layer 95 may be disposed at positions overlapping the insulator 44*a* or the insulator 44*c* in the forward-rearward direction or may be disposed rearward of the metal ring 46. In the embodiment described above, the first dense layer 92 and the second dense layer 95 are disposed at positions that are not exposed to the element chamber 33. However, at least one of the first dense layer 92 and the second dense layer 95 may be disposed at a position exposed to the element chamber 33, i.e., a position exposed to the measurement-object gas. For example, at least one of the first dense layer 92 and the second dense layer 95 may be disposed at a position located rearward of the outer porous layer 85 and exposed to the element chamber 33.

In the embodiment described above, the sensor element 20 may not include the second inner porous layer 84, and the second surface 60*b* may not be covered with the second inner porous layer 84. In this case, the sensor element 20 may not include the second dense layer 95. It is only necessary that a dense layer be disposed on at least one side surface on which connector electrodes and a porous layer are disposed (the first and second surfaces 60*a* and 60*b* in the embodiment described above) among the side surface of the element body (the first to fourth surfaces 60*a* to 60*d* in the embodiment described above). In this case, moisture is prevented from reaching the connector electrodes at least on the side surfaces on which the dense layer is disposed. Moreover, it is only necessary that the intermediate layer be disposed between the element body and the dense layer.

In the embodiment described above, the first inner porous layer 83 covers a region of the first surface 60*a* that extends from the forward end of the first surface 60*a* to its rear end except for the regions in which the first dense layer 92 and the upper connector electrodes 71 are present, but this is not a limitation. For example, the first inner porous layer 83 may cover a region extending from forward end of the first surface 60*a* to the forward ends of the upper connector electrodes 71*a* to 71*d* except for the region in which the first dense layer 92 is present. Alternatively, the first inner porous layer 83 may cover at least a region extending from the forward end of the first surface 60*a* to a position rearward of the first dense layer 92 except for the region in which the first dense layer 92 is present. The same applies to the second inner porous layer 84.

In the embodiment described above, the element body 60 has a rectangular parallelepiped shape, but this is not a limitation. For example, the element body 60 may be cylindrical or columnar. In this case, the element body 60 has one side surface.

In the embodiment described above, the gas sensor 10 detects the NOx concentration as the specific gas concentration, but this is not a limitation. The concentration of a different oxide may be used as the specific gas concentration. In the case where the specific gas is an oxide, when the specific gas itself is reduced near the measurement electrode 67, oxygen is generated, as in the embodiment described above. Therefore, the specific gas concentration can be detected based on the value that is detected by the detection portion 63 and corresponds to the oxygen. The specific gas may be a non-oxide such as ammonia. When the specific gas is a non-oxide, the specific gas is converted to an oxide, for example, near the inner main pump electrode 65 (for example, ammonia is oxidized and converted to NO). When the oxide produced by conversion is reduced near the measurement electrode 67, oxygen is generated, and the specific gas concentration can be detected based on the value that is detected by the detection portion 63 and corresponds to the oxygen. As described above, even when the specific gas is an oxide or a non-oxide, the gas sensor 10 can detect the specific gas concentration based on oxygen derived from the specific gas and generated near the measurement electrode 67.

Examples will next be described. In each Example, sensor elements were actually produced. However, the present invention is not limited to the following Examples.

Example 1

A sensor element that was the same as the sensor element 20 shown in FIGS. 2 to 4, 6, and 7 was produced, except that the gap regions 96 (the forward gap region 96a and the rear gap region 96b) were present on the second surface 60b side of the element body 60 as shown in FIG. 12 and that the protective layer 80 did not include the outer porous layer 85. The sensor element produced was used as Example 1. The sensor element 20 in Example 1 was produced as follows. First, the production step was performed as follows. Zirconia particles containing 4 mol % of yttria serving as a stabilizer, an organic binder, and an organic solvent were mixed, and the mixture was used to prepare six ceramic green sheets by tape molding. The green sheets were subjected to punching processing as needed, and patterns for the green electrodes, the green lead wires, the green connector electrodes, the green heater, the green intermediate layer, the green first dense layer, the green first inner porous layer, the green second dense layer, and the green second inner porous layer were formed by screen printing. The green first inner porous layer and the green second inner porous layer were formed using a paste prepared by mixing a raw material powder (alumina powder), a binder solution (polyvinyl acetal and butyl carbitol), a solvent (acetone), and a pore-forming material. A paste for the green first dense layer and the green second dense layer was prepared such that the porosities of the first and second dense layers 92 and 95 were 0%. Specifically, the same paste as the paste for the green first inner porous layer except that no pore-forming material was added and the amount of the solvent added was changed to adjust the viscosity was used as the paste for the green first dense layer and the green second dense layer. The green intermediate layer was formed using a paste prepared by mixing raw material powders (the alumina powder and the zirconia powder), a binder solution (polyvinyl acetal and butyl carbitol), and a solvent (acetone). No pore-forming material was added to the paste for the green intermediate layer, so that the porosity of the intermediate layer 98 was 0%. When screen printing was performed, the green first dense layer was formed by printing after the formation of the green intermediate layer such that the green intermediate layer was present between the green first dense layer and the ceramic green sheet that later became the solid electrolyte layer 78a. Then the six green sheets were stacked to obtain a layered body, and the layered body was cut to obtain small layered bodies, i.e., green sensor elements. Next, the firing step was performed in which each green sensor element was fired at 1360° C.±50° C. and the fired sensor element was cooled to room temperature (20° C.). A sensor element 20 including the element body 60, the first dense layer 92, the intermediate layer 98, etc. was thereby produced and used as a sensor element 20 in Example 1. The thickness T of the intermediate layer 98 was 5 The value of the thickness T used was the thickness T1 measured at the thinnest portion of the intermediate layer 98 (the portion located directly above the outer lead wire 75).

Examples 2 to 10 and Comparative Examples 1 to 3

Sensor elements 20 with the relations between the thermal expansion coefficients Ea, Eb, and Ec different from those in Example 1 were produced and used as Examples 2 to 10 and Comparative Examples 1 to 3. In Examples 2 to 10 and Comparative Examples 1 to 3, the solid electrolyte layers 78a to 78f were the same as those in Example 1. Specifically, the value of the thermal expansion coefficient Ea was the same for Examples 1 to 10 and Comparative Examples 1 to 3. In Examples 2 to 10 and Comparative Examples 1 to 3, the thermal expansion coefficient Eb of the first dense layer 92 was changed by selecting the raw material powder of the green dense layer from alumina, cordierite, and silicon nitride. In Examples 2 to 10 and Comparative Examples 1 to 3, the thermal expansion coefficient Ec of the intermediate layer 98 was changed by adjusting the volume ratio of the material of the raw material powder of the solid electrolyte layers 78a to 78f contained in the green intermediate layer and the volume ratio of the material of the raw material powder of the first dense layer 92 contained in the green intermediate layer. In Examples 2 to 8 and Comparative Examples 1 to 3, the thickness T of the intermediate layer 98 was set to 5 μm, which was the same as the thickness in Example 1. In Example 9, the thickness T of the intermediate layer 98 was set to 10 μm. In Example 10, the thickness T of the intermediate layer 98 was set to 1 μm. The thickness T of the intermediate layer 98 was controlled by changing the amount of the solvent contained in the paste for the green intermediate layer to thereby adjust the viscosity or adjusting the number of screen printing operations for printing the green intermediate layer.

[Measurement of Thermal Expansion Coefficients Ea to Ec]

The thermal expansion coefficients Ea to Ec in each of Examples 1 to 10 and Comparative Examples 1 to 3 were measured using the method described above. A thermomechanical analysis apparatus (type: TMA4000SA) manufactured by NETZSCH was used for the measurement.

[Evaluation of Cracking Resistance]

For each of Examples 1 to 10 and Comparative Examples 1 to 3, ten sensor elements 20 were produced, and each sensor element 20 was subjected to a test in which the sensor element 20 was exposed to high-temperature high-pressure vapor for a prescribed time to thereby evaluate cracking resistance. This test was performed using a method according to JIS A 1509-8:2014. First, the sensor element 20 was placed in an autoclave. Then the pressure inside the autoclave was gradually increased so as to reach 1 MPa or higher over about 1 hour, and the increased pressure was maintained for 1 hour or longer. Then the pressure was reduced to normal pressure as fast as possible, and the sensor element 20 was left to cool. The cooled sensor element 20 was visually checked to determine whether or not cracking occurred in the first dense layer 92. When the number of cracked sensor elements 20 out of the ten sensor element 20 was zero, the cracking resistance was rated "excellent (A)." When the number of cracked sensor elements 20 was one, the cracking resistance was rated "good (B)." When the number of cracked sensor elements 20 was two or more, the cracking resistance was rated "fail (F)." The high-temperature high-pressure state in the autoclave during the test is severer than a normal use environment of the sensor element 20 attached to a vehicle.

Table 1 summarizes the thermal expansion coefficients Ea to Ec in each of Examples 1 to 10 and Comparative Examples 1 to 3 and the results of the evaluation of the cracking resistance of the sensor elements 20. In Table 1, the values of the thermal expansion coefficients Ea to Ec are the ratios with respect to the thermal expansion coefficient Ea with the value of the thermal expansion coefficient Ea used as a reference (value: 1). Table 1 also shows the ratio Ea/Eb, the magnitude relation between Ea to Ec, the median Ed of the thermal expansion coefficient Ea and the thermal expansion coefficient Eb, the value of the left-hand side of formula (1), i.e., (Ed−0.8×(Ed−Eb)), the value of the right-hand side of formula (1), i.e., (Ed+0.8×(Ea−Ed)), whether the thermal expansion coefficients Ea to Ec satisfy formula (1), and the thickness T of the intermediate layer 98.

However, in Comparative Examples 1 and 2 in which Ea>Ec>Eb was not satisfied and in Comparative Example 3 in which the ratio Ea/Eb was more than 5.0, the evaluation of the cracking resistance of the sensor elements 20 was "fail (F)." This confirms that, when the ratio Ea/Eb is more than 1.0 and 5.0 or less and Ea>Ec>Eb is satisfied, the occurrence of cracking in the sensor element 20 can be reduced. In Examples 2 and 3 in which formula (1) was not satisfied, the evaluation of the cracking resistance was "good (B)." However, in Examples 1, 4 to 6, and 8 to 10 in which formula (1) was satisfied, the evaluation of the cracking resistance was "excellent (A)." This confirms that, when formula (1) is satisfied, the occurrence of cracking in the sensor element 20 can be further reduced. In Example 7 in which the ratio Ea/Eb was more than 3.0, the evaluation of the cracking resistance was "good (B)." However, in Examples 1, 4 to 6, and 8 to 10 in which the ratio Ea/Eb was 3.0 or less, the evaluation of the cracking resistance was "excellent (A)." This confirms that, when the ratio Ea/Eb is 3.0 or less, the occurrence of cracking in the sensor element 20 can be further reduced. The results in Example 10 confirm that the effect of reducing the occurrence of cracking is obtained when the thickness T of the intermediate layer 98 is in the range of 1 μm or more. The results in Example 9 confirm that the effect of reducing the occurrence of cracking is obtained when the thickness T of the intermediate layer 98 is in the range of 10 μm or less.

The present application claims priority based on U.S. Patent Application No. 63/211,665 filed on Jun. 17, 2021, and the entire contents of which are incorporated herein by reference.

What is claimed is:

1. A sensor element for detecting a specific gas concentration in a measurement-object gas, the sensor element comprising:

TABLE 1

| | Ratio Ea of thermal expansion coefficient of solid electrolyte layer※1 | Ratio Ec of thermal expansion coefficient of intermediate layer※1 | Ratio Eb of thermal expansion coefficient of 1st dense layer※1 | Ratio Ea/Eb | Magnitude relationship | Median Ed (=(Ea + Eb)/2) | Ed − 0.8 (Ed − Eb) | Ed + 0.8 (Ea − Ed) | Formula (1)*2 is satisfied or not | Thickness of intermediate layer T [μm] | Evaluation |
|---|---|---|---|---|---|---|---|---|---|---|---|
| Example 1 | 1 | 0.85 | 0.7 | 1.43 | Ea > Ec > Eb | 0.85 | 0.73 | 0.97 | OK | 5 | A |
| Example 2 | 1 | 0.71 | 0.7 | 1.43 | Ea > Ec > Eb | 0.85 | 0.73 | 0.97 | NG | 5 | B |
| Example 3 | 1 | 0.99 | 0.7 | 1.43 | Ea > Ec > Eb | 0.85 | 0.73 | 0.97 | NG | 5 | B |
| Example 4 | 1 | 0.75 | 0.7 | 1.43 | Ea > Ec > Eb | 0.85 | 0.73 | 0.97 | OK | 5 | A |
| Example 5 | 1 | 0.9 | 0.7 | 1.43 | Ea > Ec > Eb | 0.85 | 0.73 | 0.97 | OK | 5 | A |
| Example 6 | 1 | 0.6 | 0.35 | 2.86 | Ea > Ec > Eb | 0.68 | 0.42 | 0.94 | OK | 5 | A |
| Example 7 | 1 | 0.8 | 0.3 | 3.33 | Ea > Ec > Eb | 0.65 | 0.37 | 0.93 | OK | 5 | B |
| Example 8 | 1 | 0.95 | 0.90 | 1.11 | Ea > Ec > Eb | 0.95 | 0.91 | 0.99 | OK | 5 | A |
| Example 9 | 1 | 0.85 | 0.7 | 1.43 | Ea > Ec > Eb | 0.85 | 0.73 | 0.97 | OK | 10 | A |
| Example 10 | 1 | 0.85 | 0.7 | 1.43 | Ea > Ec > Eb | 0.85 | 0.73 | 0.97 | OK | 1 | A |
| Comparative Examples 1 | 1 | 0.7 | 0.7 | 1.43 | Ea > Ec = Eb | 0.85 | 0.73 | 0.97 | NG | 5 | F |
| Comparative Examples 2 | 1 | 1.3 | 1.5 | 0.67 | Eb > Ec > Ea | 1.25 | 1.45 | 1.05 | NG | 5 | F |
| Comparative Examples 3 | 1 | 0.6 | 0.19 | 5.10 | Ea > Ec > Eb | 0.60 | 0.27 | 0.92 | NG | 5 | F |

※1 The coefficients of thermal expansion Ea to Ec are shown as ratios to Ea with Ea as the reference (value 1).
※2 Formula (1): Ed − 0.8 × (Ed − Eb) < Ec < Ed + 0.8 × (Ea − Ed)

As can be seen from Table 1, in Examples 1 to 10 in which the ratio Ea/Eb was more than 1.0 and 5.0 or less and Ea>Ec>Eb was satisfied, the evaluation of the cracking resistance of the sensor elements 20 was "excellent (A)" or "good (B)," and the occurrence of cracking was reduced.

an elongate element body that includes a solid electrolyte layer and has a shape including at least one side surface extending in a longitudinal direction and forward and rear ends that are ends opposite to each other in the longitudinal direction;

25 at least one connector electrode that is disposed on a rear end side of any one of the at least one side surface and provided for electrical continuity with an outside of the sensor element;

a porous layer that has a porosity of 10% or more and covers at least a forward end side of the side surface on which the at least one connector electrode is disposed;

a dense layer that is disposed on the side surface so as to divide the porous layer in the longitudinal direction or to be located rearward of the porous layer, is located forward of the at least one connector electrode, and has a porosity of less than 10%;

an intermediate layer disposed at least between the dense layer and the elongate element body; and an outer lead wire, wherein the intermediate layer is located between the dense layer and the outer lead wire and covers the outer lead wire, and wherein, when thermal expansion coefficients of the solid electrolyte layer, the dense layer, and the intermediate layer in a temperature range of from 20° C. to 1360° C. are denoted by thermal expansion coefficients Ea, Eb, and Ec, respectively, a ratio Ea/Eb is more than 1.0 and less than or equal to 5.0, and Ea>Ec>Eb is satisfied.

2. The sensor element according to claim 1, wherein, when the median of the thermal expansion coefficient Ea and the thermal expansion coefficient Eb is denoted by Ed (=(Ea+Eb)/2), Ed−0.8×(Ed−Eb)<Ec<Ed+0.8×(Ea−Ed) is satisfied.

3. The sensor element according to claim 2, wherein the ratio Ea/Eb is 3.0 or less.

4. The sensor element according to claim 2, wherein the intermediate layer has a thickness T of 1 μm or more.

5. The sensor element according to claim 1, wherein the ratio Ea/Eb is 3.0 or less.

6. The sensor element according to claim 5, wherein the intermediate layer has a thickness T of 1 μm or more.

7. The sensor element according to claim 6, wherein the intermediate layer has the thickness T of 10 μm or less.

8. The sensor element according to claim 1, wherein the intermediate layer has a thickness T of 1 μm or more.

9. The sensor element according to claim 8, wherein the intermediate layer has the thickness T of 10 μm or less.

10. The sensor element according to claim 1, wherein the intermediate layer has a thickness T of 10 μm or less.

11. A gas sensor comprising the sensor element according to claim 1.

* * * * *